(12) United States Patent  
Yochum et al.

(10) Patent No.: US 11,465,922 B2
(45) Date of Patent: Oct. 11, 2022

(54) METHODS FOR ANAEROBIC WASTE DIGESTION

(71) Applicant: Trane International Inc., Davidson, NC (US)

(72) Inventors: Charles Don Yochum, Marietta, GA (US); Stanley Scott Selman, Auburn, AL (US); Nathalie Shaffer, Atlanta, GA (US)

(73) Assignee: Trane International Inc., Davidson, NC (US)

( * ) Notice: Subject to any disclaimer, the term of this patent is extended or adjusted under 35 U.S.C. 154(b) by 0 days.

(21) Appl. No.: 17/156,250

(22) Filed: Jan. 22, 2021

(65) Prior Publication Data

US 2021/0171376 A1 Jun. 10, 2021

Related U.S. Application Data

(63) Continuation of application No. 16/704,750, filed on Dec. 5, 2019, now Pat. No. 10,899,640.

(51) Int. Cl.
C02F 3/28 (2006.01)
C02F 11/04 (2006.01)
(Continued)

(52) U.S. Cl.
CPC ............ *C02F 3/2813* (2013.01); *C02F 1/463* (2013.01); *C02F 3/284* (2013.01); *C02F 3/2806* (2013.01);
(Continued)

(58) Field of Classification Search
CPC ...... C02F 3/2813; C02F 1/463; C02F 3/2806; C02F 3/284; C02F 11/04; C02F 2001/007;
(Continued)

(56) References Cited

U.S. PATENT DOCUMENTS 3,933,638 A 1/1976 Varani
4,022,665 A 5/1977 Ghosh et al.
(Continued)

FOREIGN PATENT DOCUMENTS

CA 3023182 11/2017
EP 1354940 10/2003
(Continued)

*Primary Examiner* — Fred Prince
(74) *Attorney, Agent, or Firm* — Hamre, Schumann, Mueller & Larson, P.C.

(57) ABSTRACT

Methods for generating methane from animal waste by anaerobic digestion using bacteria. A screen separator removes suspended solids greater in size than a predetermined size ranging from about 50μ to about 150μ. An electrocoagulation unit electrochemically hydrolyses the waste, causing particles to settle out. A dissolved carbon air flotation has a $CO_2$ bubbler for separating large particles from small particles by flotation. An anaerobic digester produces biogas. The digester has a biocurtain for growing the bacteria and a heat exchanger for heating the bacteria. The biocurtain surface is convoluted to retain the bacteria. A membrane module removes $CO_2$. A knock out pot for removes droplets of water. A scrubber removes water vapor, particulates, and contaminant gas. A compressor boosts pressure. A gas chromatograph monitors the biogas composition. A flare skid lowers excess pressure for safety. Biogas is injected into a local pipeline system. A process control is used for controlling the anaerobic waste digestion system.

18 Claims, 22 Drawing Sheets

(51) Int. Cl.
*C02F 1/46* (2006.01)
*C12M 1/107* (2006.01)
*C02F 1/463* (2006.01)
*C12M 1/00* (2006.01)
*C02F 1/00* (2006.01)
*C02F 103/22* (2006.01)
*C02F 103/20* (2006.01)
*C12M 1/33* (2006.01)

(52) U.S. Cl.
CPC ............ *C02F 11/04* (2013.01); *C12M 21/04* (2013.01); *C12M 47/10* (2013.01); *C02F 2001/007* (2013.01); *C02F 2103/20* (2013.01); *C02F 2103/22* (2013.01); *C02F 2203/006* (2013.01); *C02F 2303/06* (2013.01); *C02F 2303/24* (2013.01); *C12M 45/02* (2013.01); *Y02E 50/30* (2013.01); *Y02W 10/20* (2015.05)

(58) Field of Classification Search
CPC ............ C02F 2103/20; C02F 2103/22; C02F 2203/006; C02F 2303/06; C02F 2303/24; C12M 21/04; C12M 47/10; C12M 45/02; Y02E 50/30; Y02W 10/20
USPC .... 210/603, 612, 613, 614, 615, 748.1, 175, 210/252, 259, 906
See application file for complete search history.

(56) References Cited

U.S. PATENT DOCUMENTS

| | | |
|---|---|---|
| 4,040,953 A | 8/1977 | Ort |
| 5,529,692 A | 6/1996 | Kubler |
| 5,593,590 A | 1/1997 | Steyskal |
| 5,746,919 A | 5/1998 | Cague et al. |
| 6,139,710 A | 10/2000 | Powell |
| 6,254,775 B1 | 7/2001 | McElvaney |
| 6,291,232 B1 | 9/2001 | Miller, III |
| 6,342,378 B1 | 1/2002 | Zhang et al. |
| 6,905,600 B2 | 6/2005 | Lee, Jr. |
| 7,045,063 B2 | 5/2006 | Zhang et al. |
| 7,160,472 B2 | 1/2007 | Van Vliet et al. |
| 7,297,274 B2 | 11/2007 | Wilkie |
| 7,445,707 B2 | 11/2008 | Menke et al. |
| 8,480,901 B2 | 7/2013 | Johnson |
| 9,090,496 B2 | 7/2015 | Lugo et al. |
| 9,988,646 B2 | 6/2018 | Pidaparti et al. |
| 2002/0079266 A1 | 6/2002 | Ainsowrth et al. |
| 2005/0000906 A1 | 1/2005 | Blais et al. |
| 2006/0060526 A1 | 3/2006 | Binning et al. |
| 2008/0020456 A1 | 1/2008 | Choate et al. |
| 2010/0252498 A1* | 10/2010 | Ott .......................... C02F 9/00 210/205 |
| 2013/0327694 A1 | 12/2013 | Crewry et al. |
| 2013/0341267 A1 | 12/2013 | Prasad et al. |
| 2015/0008181 A1 | 1/2015 | Bassani et al. |
| 2016/0002582 A1 | 1/2016 | Lin et al. |
| 2016/0096757 A1 | 4/2016 | Wright |

FOREIGN PATENT DOCUMENTS

| | | |
|---|---|---|
| EP | 3180971 | 6/2017 |
| WO | 2010094115 | 8/2010 |
| WO | 2012103629 | 8/2012 |
| WO | 2012155086 | 11/2012 |
| WO | 2016065400 | 5/2016 |
| WO | 2017158461 | 9/2017 |
| WO | 2018136019 | 7/2018 |
| WO | 2018156940 | 8/2018 |

* cited by examiner

SEPARATING SOLIDS-PHASE 1

EC

GAS PRODUCTION PHASE 4

EFFLUENT FLOW PHASE 4 PARALLEL
FIRST LSAD OPEN - SECOND LSAD OPEN

EFFLUENT FLOW PHASE 4 MAINTENANCE
FIRST LSAD OPEN - SECOND LSAD CLOSED

EFFLUENT FLOW PHASE 4 MAINTENANCE
FIRST LSAD CLOSED - SECOND LSAD OPEN

EFFLUENT FLOW PHASE 4 SERIES
FIRST LSAD 1st FLOW - SECOND LSAD 2nd FLOW

EFFLUENT FLOW PHASE 4 SERIES
SECOND LSAD 1st FLOW - FIRST LSAD 2nd FLOW

GAS UPGRADE PHASE 5

PIPELINE INJECTION
PHASE 6

METHODS FOR ANAEROBIC WASTE DIGESTION

CROSS-REFERENCE TO RELATED APPLICATION

This application is a Continuation of U.S. Utility patent application Ser. No. 16/704,750 entitled "ANAEROBIC WASTE DIGESTION SYSTEM" and filed Dec. 5, 2019, now U.S. Pat. No. 10,899,640, the entirety of which is hereby incorporated by reference herein for all purposes.

TECHNICAL FIELD

The presently disclosed technologies are directed to an apparatus and method for processing agricultural waste, and in particular, an apparatus and method for generating high purity methane from agricultural animal waste by anaerobic digestion.

BACKGROUND

Anaerobic digestion is a naturally-occurring biological process. It provides energy for certain cells necessary to sustain life. This natural biological process has been employed to remove contaminants from waste water for more than 100 years.

Some of the benefits of anaerobic digestion include the capability for processing hard-to-digest natural organic compounds. The process is also able to decompose toxic compounds such as solvents, degreasers, cleaners, paints and coatings.

The process can remove undesirable organisms found in clarifiers used reduce turbidity in municipal waste water. It further allows reducing the water content of waste sludge, thereby reducing the volume of sludge. Volatile components of sludge, undesirable odors, and pathogens are also reduced. As a byproduct, biosolids are useful as soil conditioners. All these benefits are accompanied by a reduction in sludge handling and disposal costs.

Anaerobic digestion also produces high quality methane, the main component of natural gas. However, methane production has not been a compelling reason to utilize anaerobic digesters to process waste water, because it is a more costly method of producing methane than other known methods such as extraction from oil and gas wells. Thus, commercial anaerobic digesters typically focused on the non-energy generation benefits, chiefly cost savings proportionate to the amount of waste produced.

Anaerobic digestion may also be used in industrial processes such as pulp and paper, food and beverage, and municipal wastewater treatment. For dairy farms, as well as other livestock farms, the implementation of anaerobic digestion may have advantages, such as cost savings from improved process efficiency. In addition, many modern farms would justify the use of anaerobic digestion to process livestock waste if sufficient efficiencies were achievable to generate additional income from the sale of generated methane fuel. A highly-efficient and economically-viable methane generation technique would be a welcome advance in the art.

SUMMARY

In one aspect, an anaerobic waste digestion system is used in connection with a source of agricultural animal waste. Methane is generated from the animal waste by anaerobic digestion using bacteria. The waste is a water-based slurry having solid particles larger than a predetermined size unsuitable for digestion. The slurry also has solid particles smaller than the predetermined size suitable for digestion.

The anaerobic waste digestion system comprises a first phase particle separator, including a screen separator that receives the slurry. The screen separator removes suspended solids greater in size than the predetermined size. The first phase particle separator allows passage through the separator of the slurry.

A second phase particle separator includes an electrocoagulation unit connected in fluid communication with the screen separator. The electrocoagulation unit electrochemically induces particle destabilization of the slurry. This will cause particles to settle out of the slurry. The electrocoagulation unit allows passage through the electrocoagulation unit of the slurry.

A third phase particle separator includes a dissolved carbon air flotation separator connected in fluid communication with the electrocoagulation unit. The dissolved carbon air flotation separator includes a $CO_2$ bubbler for separating by flotation the particles larger than the predetermined size from the particles smaller than the predetermined size. Particles with high mass, or sludge, also settle and are separated. The dissolved carbon air flotation separator allows passage through the separator of the particles smaller than the predetermined size as feedstock. Because the slurry particles are not of uniform density or size, and the smallest particles are preferred for digestion, the cross-sectional flow area of adjustable baffles are adjusted to regulate the flow rate (and velocity) of the influent slurry. Hence, small particles travel through the separation zones and are sent to the digester. Large particles of greater density will follow a trajectory downward into the sludge hopper because of their weight. Large particles of lesser density will be buoyed by the $CO_2$ and float upward to the skim conveyer.

A fourth phase gas producer includes at least one low solids anaerobic digester connected in fluid communication with the dissolved carbon air flotation separator. Influent enters the anaerobic digester as feedstock, and biogas exits as a product. Effluent exits as wastewater, and slurry exits as settled solids. The digester includes a heat exchanger for heating the bacteria. The digester includes at least one biocurtain adjacent the heat exchanger for growing the bacteria. The biocurtain includes at least one surface convoluted so as to retain the bacteria. The anaerobic digester allows passage through the digester of the biogas.

A fifth phase gas refiner includes a membrane module connected in fluid communication with the anaerobic digester. The membrane module removes $CO_2$ and contaminant liquids. The fifth phase gas refiner allows passage through the gas refiner of the pipeline quality natural gas. Rejected $CO_2$ is sent upstream to be used in the above-described processes.

A sixth phase pipeline injector injects the biogas into a local pipeline system. The sixth phase pipeline injector is connected in fluid communication with the membrane module.

A process control is operatively connected to the anaerobic waste digestion system. The process control is used for controlling the anaerobic waste digestion system.

The predetermined particle size ranges from about 10μ to about 150μ.

In another aspect, a method is disclosed for generating methane from animal waste by anaerobic digestion, and is used in connection with a source of agricultural animal waste. The waste is a water-based slurry having solid particles larger than a predetermined size unsuitable for digestion. The slurry also has solid particles smaller than the predetermined size, which are suitable for digestion. The method comprises providing a first phase particle separator downstream of the source of agricultural animal waste. A screen separator is juxtaposed with the first phase particle separator. The slurry is received into the screen separator, and suspended solids that are greater in size than the solid particles predetermined size are removed with the screen separator. The slurry is then allowed passage through first phase particle separator.

A second phase particle separator is provided downstream of the first phase particle separator. An electrocoagulation unit is juxtaposed with the second phase particle separator. The electrocoagulation unit is connected in fluid communication with the screen separator. The slurry is received into the electrocoagulation unit. The slurry is electrochemically hydrolyzed and destabilized with the electrocoagulation unit. This will cause the solid particles to settle out of the slurry. The slurry is then allowed passage through the electrocoagulation unit.

A third phase particle separator is provided downstream of the second phase particle separator. A dissolved carbon air flotation separator is juxtaposed with the third phase particle separator. The dissolved carbon air flotation separator is connected in fluid communication with the electrocoagulation unit. The slurry is received into the dissolved carbon air flotation separator. $CO_2$ bubbles are then introduced into the dissolved carbon air flotation separator. The solid particles larger than the predetermined size are separated by flotation from the solid particles smaller than the predetermined size with the $CO_2$ bubbles. High mass particles, or sludge, settle to the bottom, and are collected. The solid particles smaller than the solid particles predetermined size are then allowed passage through the dissolved carbon air flotation separator as feedstock.

A fourth phase gas producer is provided downstream of the third phase particle separator. At least one low solids anaerobic digester is juxtaposed with the fourth phase gas producer. The anaerobic digester is connected in fluid communication with the dissolved carbon air flotation separator. Influent is received into the anaerobic digester as feedstock. Methane biogas is produced by anaerobically digesting the feedstock with bacteria. At least one biocurtain is disposed within the digester. The bacteria is grown on at least one surface of the biocurtain. A heat exchanger is juxtaposed with the biocurtain. The bacteria is then heated with the heat exchanger. The biogas is allowed passage through the anaerobic digester as a product. Effluent is allowed passage through the anaerobic digester as wastewater.

A fifth phase gas refiner is provided downstream of the fourth phase gas producer. A membrane module is juxtaposed with the fifth phase gas refiner. The membrane module is connected in fluid communication with the anaerobic digester. Heavy hydrocarbons, $CO_2$, and contaminant liquids are removed with the membrane module. The pipeline quality natural gas is allowed passage through fifth phase gas refiner.

A process control is provided, and is operatively connected to the anaerobic waste digestion system. The anaerobic waste digestion system is controlled with the process control.

The slurry having the predetermined solid particle size ranging from about 10μ to about 150μ is processed with the anaerobic waste digestion system.

These and other aspects, objectives, features, and advantages of the disclosed technologies will become apparent from the following detailed description of illustrative embodiments thereof, which is to be read in connection with the accompanying drawings.

BRIEF DESCRIPTION OF THE DRAWINGS

Various embodiments of the disclosed system and method are described herein with reference to the drawings wherein.

Figure 1:
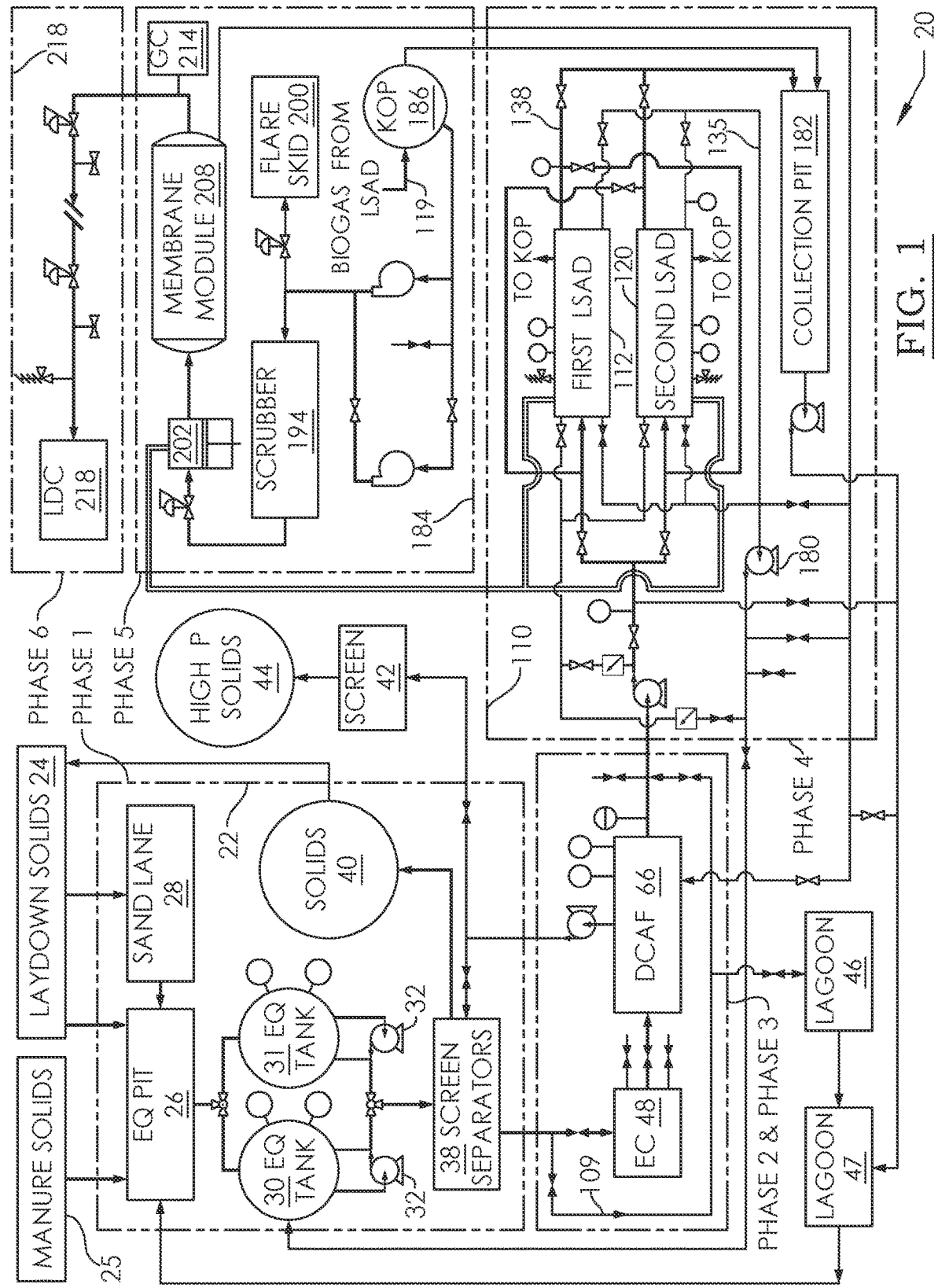
FIG. 1 is a piping and instrumentation schematic diagram of an exemplary anaerobic waste digestion system constructed in accordance with the present disclosure.

The various aspects of the present disclosure mentioned above are described in further detail with reference to the aforementioned figures and the following detailed description of exemplary embodiments. It should be noted that drawings herein are not to scale.

DETAILED DESCRIPTION

As used herein, comminution refers to the reduction of solid materials from one average particle size to a smaller average particle size, by crushing, grinding, cutting, vibrating, or other processes, so as to reduce the size and to increase the surface area of solids.

As used herein, LDC refers to Local Distribution Company (pipeline system).

As used herein, RNG refers to Renewable Natural Gas, which is pipeline quality, 95%-98% pure methane.

As used herein, LSAD refers to Low Solids Anaerobic Digester, which is a continuous feed, fixed film design digester.

As used herein, DCAF refers to Dissolved Carbon Air Flotation.

As used herein, EC refers to Electrocoagulation, or electrochemically induced hydrolysis and particle separation.

As used herein, VS refers to Volatile Solids, which is the amount of OM (organic matter) in manure slurry. Volatile Solids analysis determines the total amount of OM in the slurry on a dry mass basis. The slurry should be 60 percent or more VS on a dry mass basis, as non-volatile solids will not contribute to methane production.

As used herein, OD refers to Oxygen Demand, which is used to estimate the energy content of organic matter. Organic matter with high energy content produces more methane than OM with low energy content.

As used herein, COD refers to Chemical Oxygen Demand, which is generally used to determine OD (oxygen demand) for anaerobic digestion. A COD test measures OM in the absence of oxygen. COD will vary by dilution with water, but preferably is greater than 15,000 mg/ml, that is, mg of OM per ml of slurry.

As used herein, OLR refers to Organic Loading Rate, which is how much VS is fed into or loaded per day into a digester. OLR and methane generation are directly proportional.

As used herein, SRT refers to Solids Residence Time, and is the length of time the solid particles stay in the digester. SRT is directly related to Organic Loading Rate, due to the high concentration of organics present in the solids entering the digester.

As used herein, HRT refers to Hydraulic Residence Time, and is the digester's wetted volume divided by the flow rate of the wastewater passing through the digester. It represents the bulk measure of time between influent flow entering and effluent flow exiting the digester.

As used herein, KOP refers to Knock Out Pot, a process apparatus that removes excess water from the gas. Also known as a flash drum, the KOP prevents entrained droplets of water, liquids and particulates from reaching downstream process equipment.

As used herein, GC refers to Gas Chromatography.

As used herein, EQ refers to equalization. EQ Pit refers to a concrete pit adjacent to the screens. It is a holding pit for eventual discharge to the EQ tanks.

As used herein, slurry refers to a combination of large, mid-sized, and small solid waste particles, suspended in water. Slurry is the flowing effluent material before non-contributing particle solids are removed, and before digestion releases methane gas.

As used herein, feedstock refers to manure wastewater that has passed through the three separation phases, and has a small average particle size ideal for digestion. Effluent leaving the DCAF and entering the LSAD is feedstock.

As used herein, PET refers to polyethylene terephthalate.

As used herein, the instruments are defined as follows: LSH refers to Level Sensor High; LSL refers to Level Sensor Low; pH refers to Acid/Base Sensor; TI refers to Temperature Indicator; PI refers to Pressure Indicator; DP refers to Differential Pressure Sensor.

As used herein, micron is a unit of linear measurement equal to one thousandth of a millimeter, or one millionth of a meter. The micron symbol is µ.

As used herein, the word "exemplary" means "serving as an example, instance, or illustration." Any embodiment described herein as "exemplary" is not necessarily to be construed as preferred or advantageous over other embodiments. The word "example" may be used interchangeably with the term "exemplary."

Describing now in further detail these embodiments with reference to the Figures as described above, FIG. 1 depicts an exemplary Anaerobic Waste Digestion System 20 having at least six distinct process phases. The first three phases each comprise a particle separation process. The fourth phase is gas production by anaerobic digestion. The fifth phase is a further refinement or gas upgrade process by means of a gas scrubbing apparatus. The sixth phase is an injection phase wherein the gas is checked for quality, then injected into a pipeline.

Figure 2:
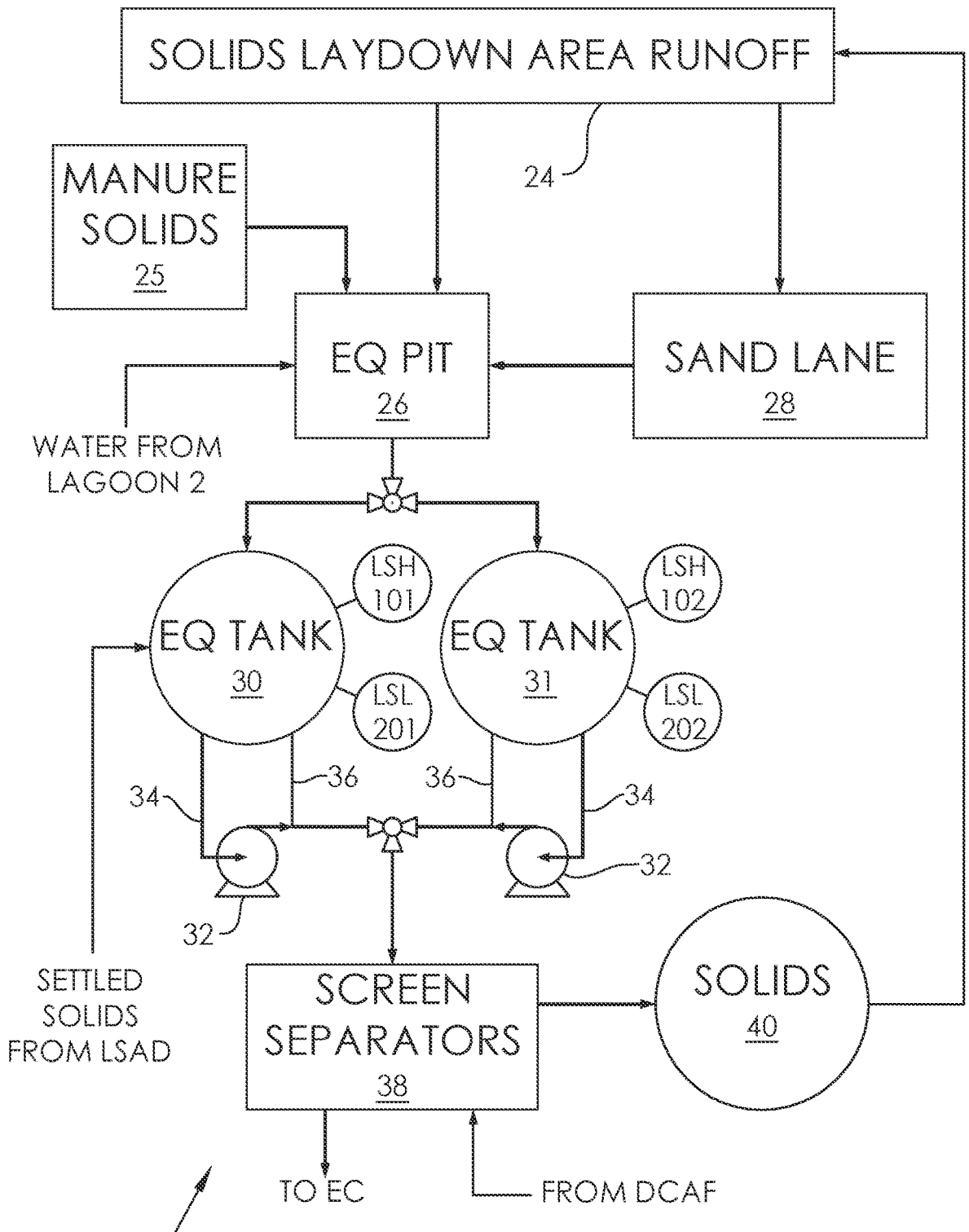
FIG. 2 is an enlarged detail schematic diagram of the collection and first separation phase of the anaerobic waste digestion system of FIG. 1.

FIG. 2 shows the first phase 22 of the particle separation process, the first phase particle separator 22. Process water from the lagoon and urine mix with solid manure from the freestall floor. The resulting liquid slurry runoff enters a washdown area, the solids laydown area 24. This material flows by gravity into an EQ pit 26. An additional laydown area, the manure solids area 25, allows the addition of solid manure and associated wastes from other sources, such as feedlots, milking operations, composting, and outside sources of animal waste from neighboring farms. The manure solids 25 also enter the EQ pit 26.

Sand is commonly used in dairy farms for bedding cows. A high volume of recycled water from the lagoons 41, 42, is added to the sand, and the mixture of sand and solid manure is directed into a long, narrow trough called a sand lane 28. The water dilutes the manure and allows the sand to settle out on the bottom of the sand lane 28. The sand is periodically removed, washed, dried, and reused as bedding. Other methods of sand separation are known in the prior art, and the sand lane is non-limiting. The diluted manure slurry, free of sand, flows into the EQ pit 26. Rain and snow fall on livestock yards and outdoor confinement areas, adding to the process flow. However, most of the process water comes from the lagoons 41, 42.

From the EQ pit 26, slurry enters two EQ tanks 30, 31 by gravity flow. One EQ tank 30 is filling up while the other EQ tank 31 is discharging through slurry pump inlet 34 to the slurry pump 32. Then the flow is changed, and EQ tank 31 is filling up while the other EQ tank 30 is discharging through slurry pump inlet 34 to the slurry pump 32. Alternating in this manner provides a nearly continuous flow. Output from the slurry pump 32 is sent to the screen separators 38. A portion of the slurry pump 32 output is diverted through slurry recirculation 36 back to EQ tanks 30, 31. This serves to agitate the slurry, so as to prevent settling out of solids in the EQ tanks 30, 31. The solids are subjected to high shear forces within the recirculation slurry pump 32. This action breaks down large particles, reducing particle size by hydraulic shear, and releases organic particles, thereby increasing available COD. A portion of the settled solids are recirculated back from the downstream fixed film digester LSAD, as described hereinbelow.

Anaerobic Waste Digestion System 20 relies mostly upon gravity flow to convey slurry and other fluids from any apparatus or tank at a given elevation, to a downstream apparatus or tank situated at a lower elevation. At any points in the process where gravity is insufficient to maintain the process flow, pumps are utilized, as shown in the drawing figures.

The wash-down is identified and separated by particle size to optimize the anaerobic digestion process and produce the maximum amount of methane yield per pound of feedstock. Settled-out (sand removed) manure wash-down is a slurry of varying-sized particles. The particle size varies from less than 1μ up to approximately 1500μ. Particles of about 150μ and larger are ideal for land application. Particles less than about 150 μ are preferred for further processing for methane production. The transition size between efficient digestion and non-efficient digestion ranges from about 50μ to about 150μ. The preferred particle size of less than about 150μ used herein shall be considered non-limiting.

Embodiments in accordance with the present disclosure will separate large particles from small particles, and anaerobically digest the small size particles having high VS to maximize methane production. In this particle separation first phase 22, up to approximately 70% of large suspended solids, typically >750μ, are separated through a vertical screen separator 38, and removed to the solids tank 40. High phosphorus solids are removed by screen separator 42 to the high phosphorus solids tank 44. The solids removed by screen separator 38 are dairy manure particles that are too large to be digested.

Figure 3:
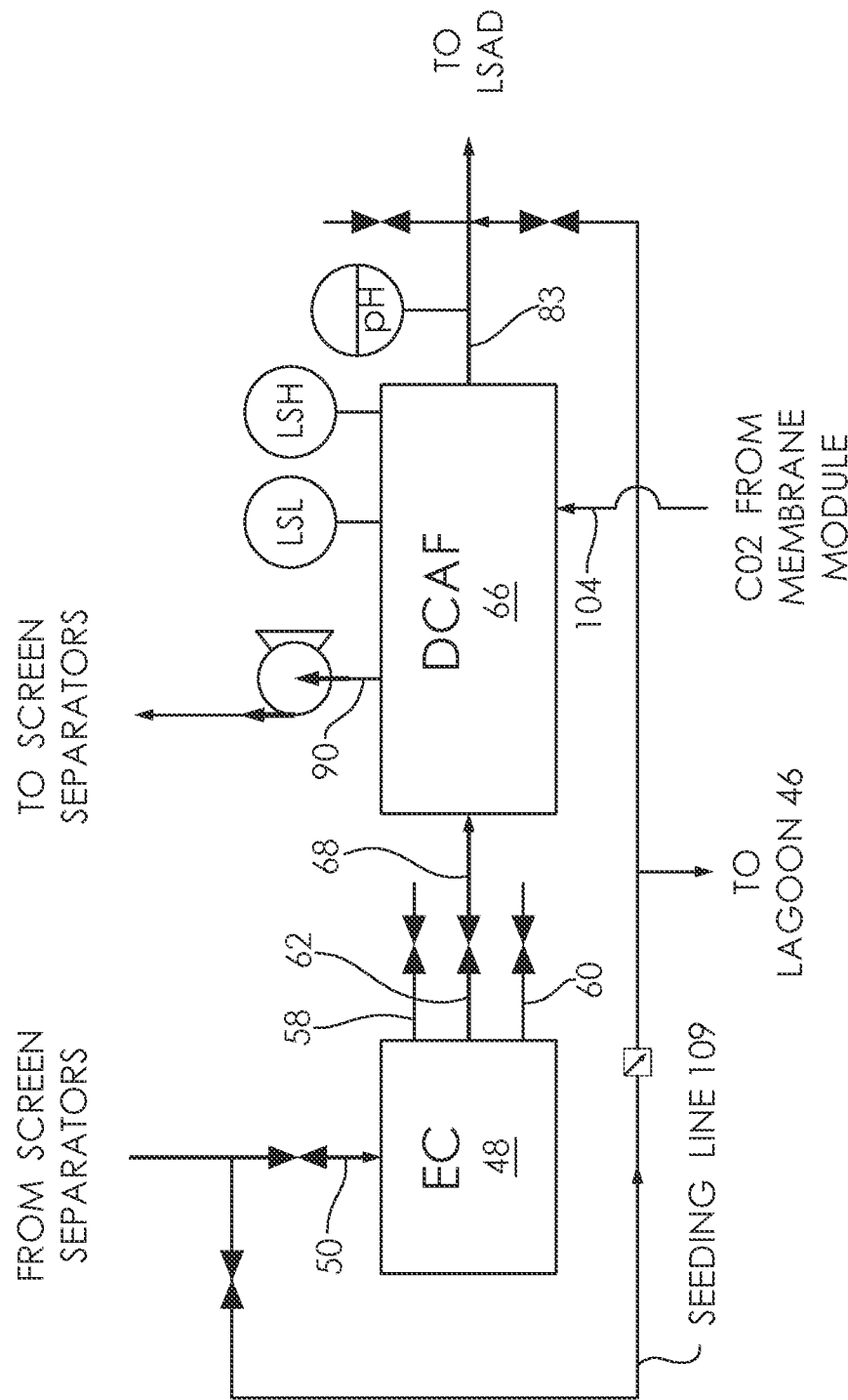
FIG. 3 is an enlarged detail schematic diagram of the second and third separation phases of the anaerobic waste digestion system of FIG. 1.
Figure 4:
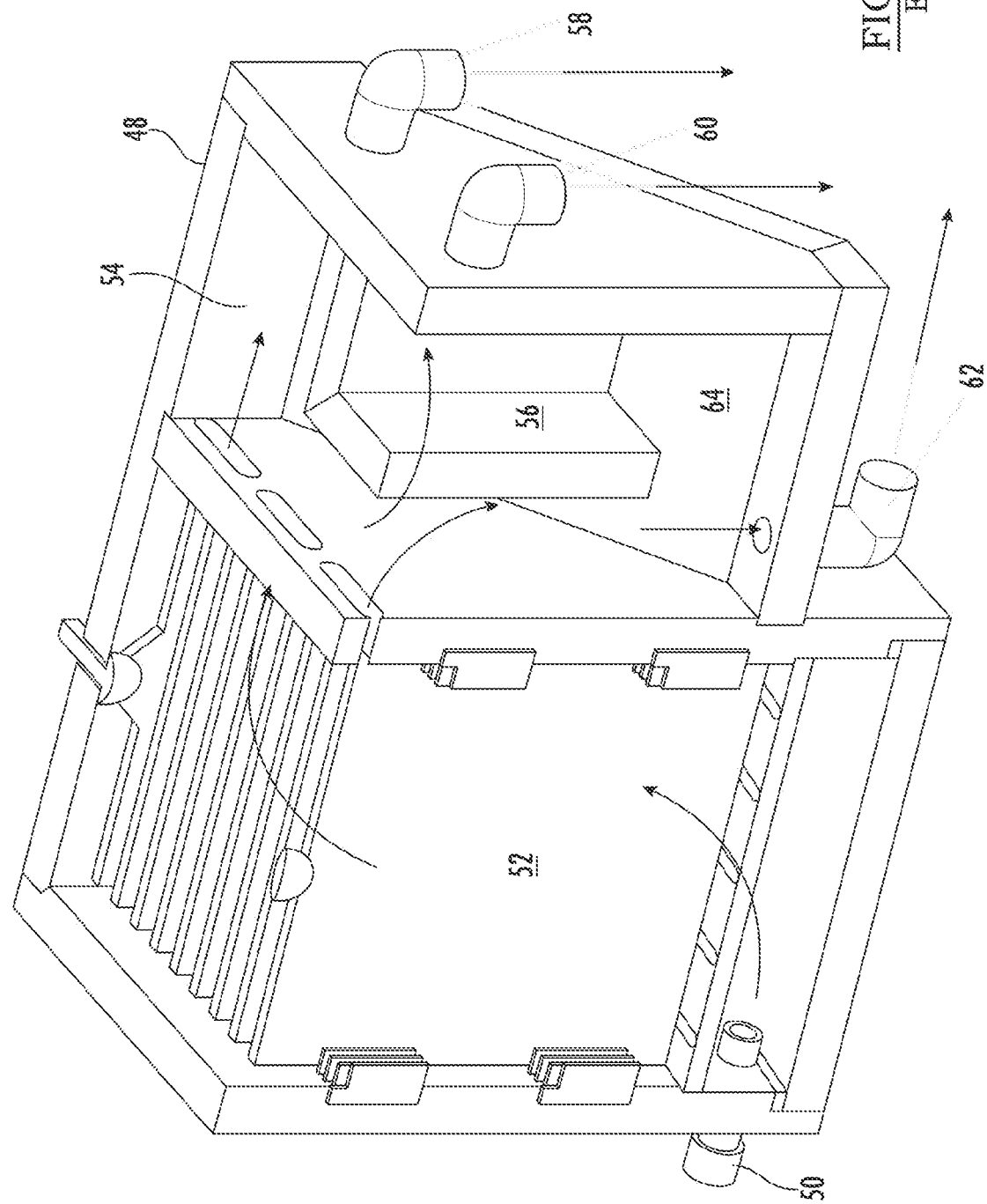
FIG. 4 is a cutaway front elevational perspective view of the second separation phase Electrocoagulation (EC) of the anaerobic waste digestion system of FIG. 1.
Figure 5:
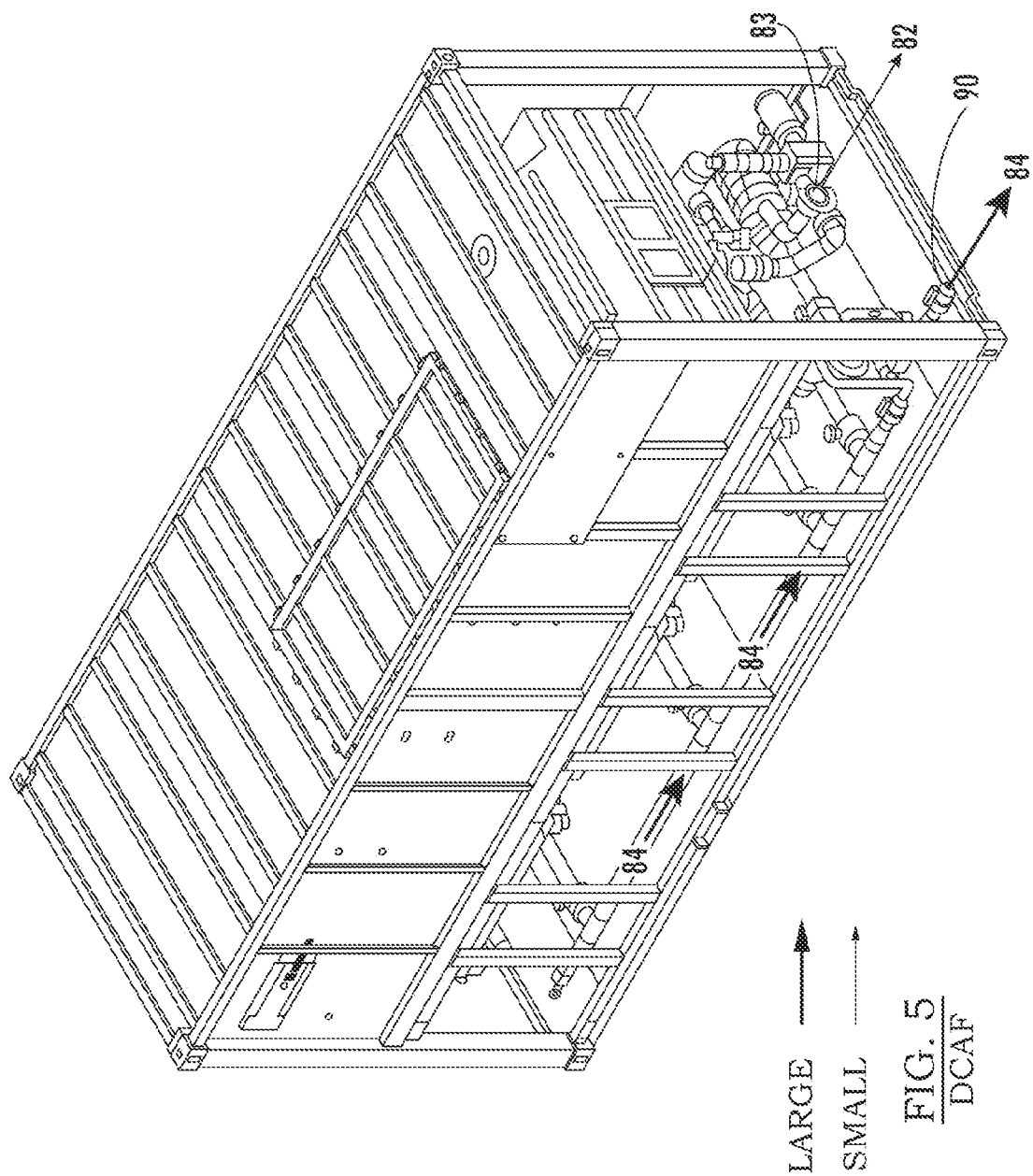
FIG. 5 is an outside front elevational perspective view of the third separation phase Dissolved Carbon Air Flotation (DCAF) of the anaerobic waste digestion system of FIG. 1, as seen from the outlet end.

Referring now to FIGS. 3-8, as well as FIGS. 1 and 2, the second and third phase of the particle separation process are shown. FIGS. 3 and 4 show the second phase 48 of the particle separation process, which is the EC or Electrocoagulation particle separator 48, wherein electrochemically induced hydrolysis of the slurry occurs. The slurry enters an inlet 50 and passes between low voltage metal electrode plates 52, creating ions from the water and the electrodes. The ions destabilize the binding force holding the solids in suspension, thereby causing particles of every size to settle out of the slurry. The ions further introduce a small amount of ionic iron which makes certain compounds insoluble. These compounds float out and are removed at a later phase. Electrochemical sanitation of the washdown slurry in the EC 48 occurs concurrently, and reduces pathogens such as viruses, enterococcus, and fecal coliform prior to digestion.

The EC 48 destabilizes solids in the effluent, causing them to fall out of suspension. Settling is directly proportional to the particle size and mass. Particles of greater mass will settle at a higher velocity than particles of lesser mass. Prior art EC utilizes a weir to separate out the floating solids, and is open at the top to exhaust hydrogen gas. In contrast, the EC 48 disclosed herein eliminates the weir, and all destabilized solids travel immediately into the collection basin 54. The separation of the destabilized solids occurs downstream, as disclosed hereinbelow.

The collection basin has three outlets, which are utilized for tuning the EC system for optimal Electrochemical separation. Each outlet is spaced apart vertically to separate solids based on their settling velocities. The smallest particles settle slowly, and hence travel directly to the high outlet 58. The mid-sized particles settle more rapidly than the small particles, and will travel around the internal baffle 56 to the mid outlet 60. The largest particles will settle the most rapidly, moving quickly to the sloping floor 64 of the collection basin 54, then through the low outlet 62. The EC port low outlet 62 is the primary discharge for all of the flows. The high outlet 58 and the mid outlet 60 are primarily used for particle size measurements to tune the EC 48. Power levels to the electrode plates 52 are adjusted to render the smallest size particles at the low outlet 62.

The EC 48 of the present disclosure operates at a lower power level than that of the prior art. The lower power results in a slower overall flow rate of slurry, which allows finer control of the particle settling. The slower flow rate reduces hydrogen formation to near zero, allowing the EC to be covered. Electrochemically induced particle separation produces hydrolysis, which accelerates methane generation. Hydrolysis is a rate-limiting step in anaerobic digestion.

Referring now to FIGS. 5-8, as well as FIGS. 1-3, the third phase 66 of the particle separation process is the DCAF 66 or dissolved carbon air flotation particle separator 66. Prior-art devices are known as dissolved air flotation, and use air, which inhibits anaerobic digestion, to float out larger particles. The DCAF 66 disclosed herein uses $CO_2$ from a downstream scrubbing process described hereinbelow, to remove larger particles including phosphorus, and other non-methane-contributing particles such as silica (sand). $CO_2$ in the DCAF 66 is dissolved in the effluent water, which is carried downstream into the digestion process. Exogenous $CO_2$ has been demonstrated to increase methane generation. The Anaerobic Waste Digestion System 20 recycles $CO_2$, thereby reducing greenhouse gas emissions.

Influent flow 72 enters the influent inlet 68 and flows through the influent manifold 70. The influent flow 72 travels upward and then laterally through at least one, and preferably a plurality of adjusting baffles 74. The influent flow 72 then enters the separation zone 76, where large, heavy particles of sludge flow 84 settle downward through the sludge hopper 86 and enter the sludge manifold 88. Sludge flow 84 exits the DCAF 66 by the sludge outlet 90.

The adjusting baffles 74 each are able to be adjusted for cross-sectional flow area, so as to regulate the flow rate of the influent flow 72. In this manner, the hydrodynamic trajectory of the influent particles and the residence time in the separation zone 76 will be adjusted to cause heavy particles to separate from the influent flow 72 and move downward. Smaller, lighter particles, less than about 150μ, will flow through the separation zone 76 and into the clear well 80. Effluent flow 82, now containing small particles, will exit the DCAF 66 by the effluent outlet 83. A pH meter will monitor effluent flow 82. The seeding line 109 is used to convey seed bacteria to the effluent outlet 83 to maintain an active bacteria culture for digestion further downstream. In the event that there is an issue downstream of the DCAF 66, effluent flow 82 exiting the DCAF 66 can be diverted to the first lagoon 46 to be stored and recycled for process water. In the event that heavy particles are found in the effluent flow 82 exiting the DCAF 66 at the DCAF effluent outlet 83, a counter flow can be diverted through the seeding line 109 to lagoon 46 for recycling, as shown in FIG. 3.

Figure 6:
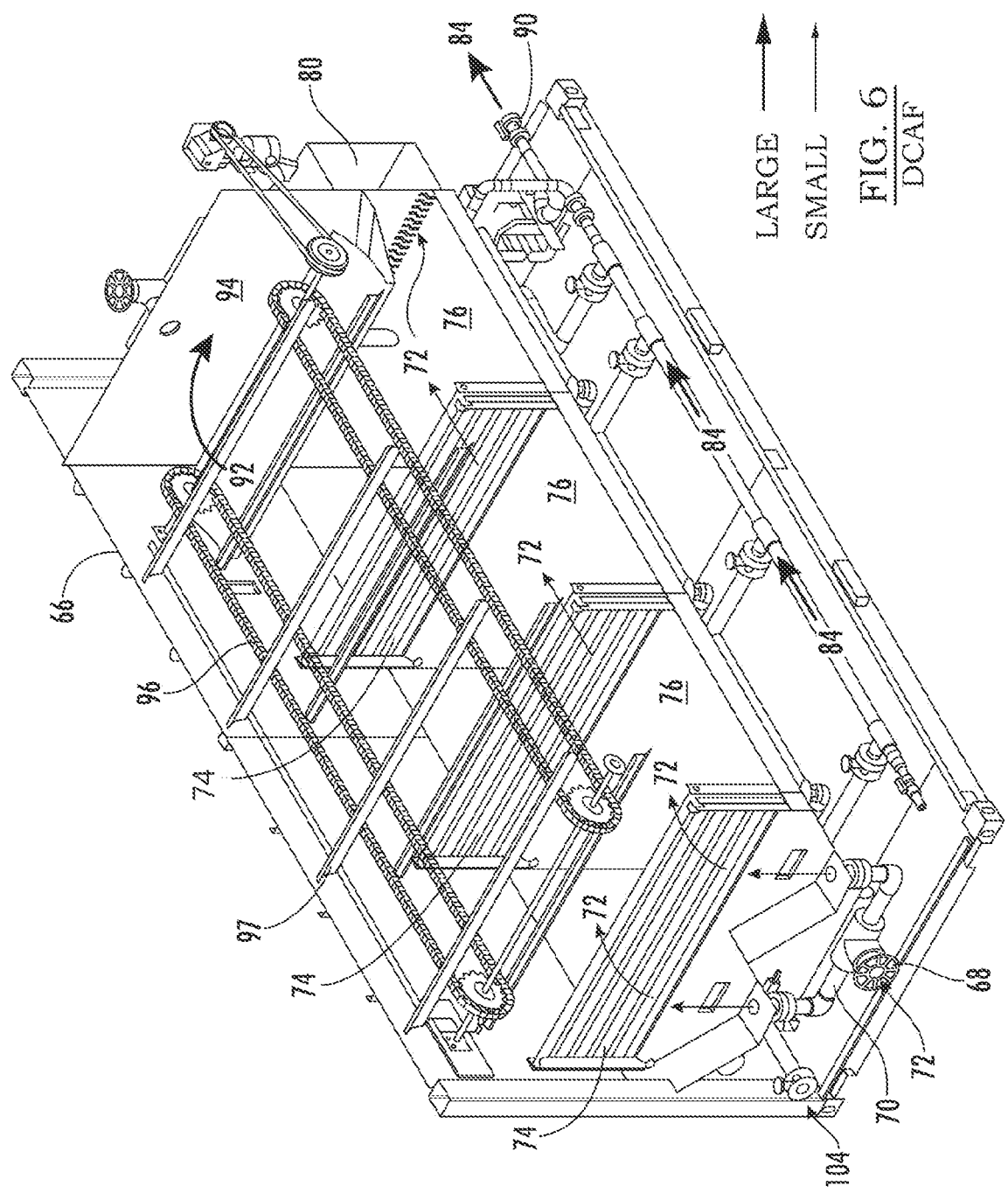
FIG. 6 is a cutaway front elevational perspective view of the third separation phase Dissolved Carbon Air Flotation (DCAF) of the anaerobic waste digestion system of FIG. 1, as seen from the inlet end.
Figure 7:
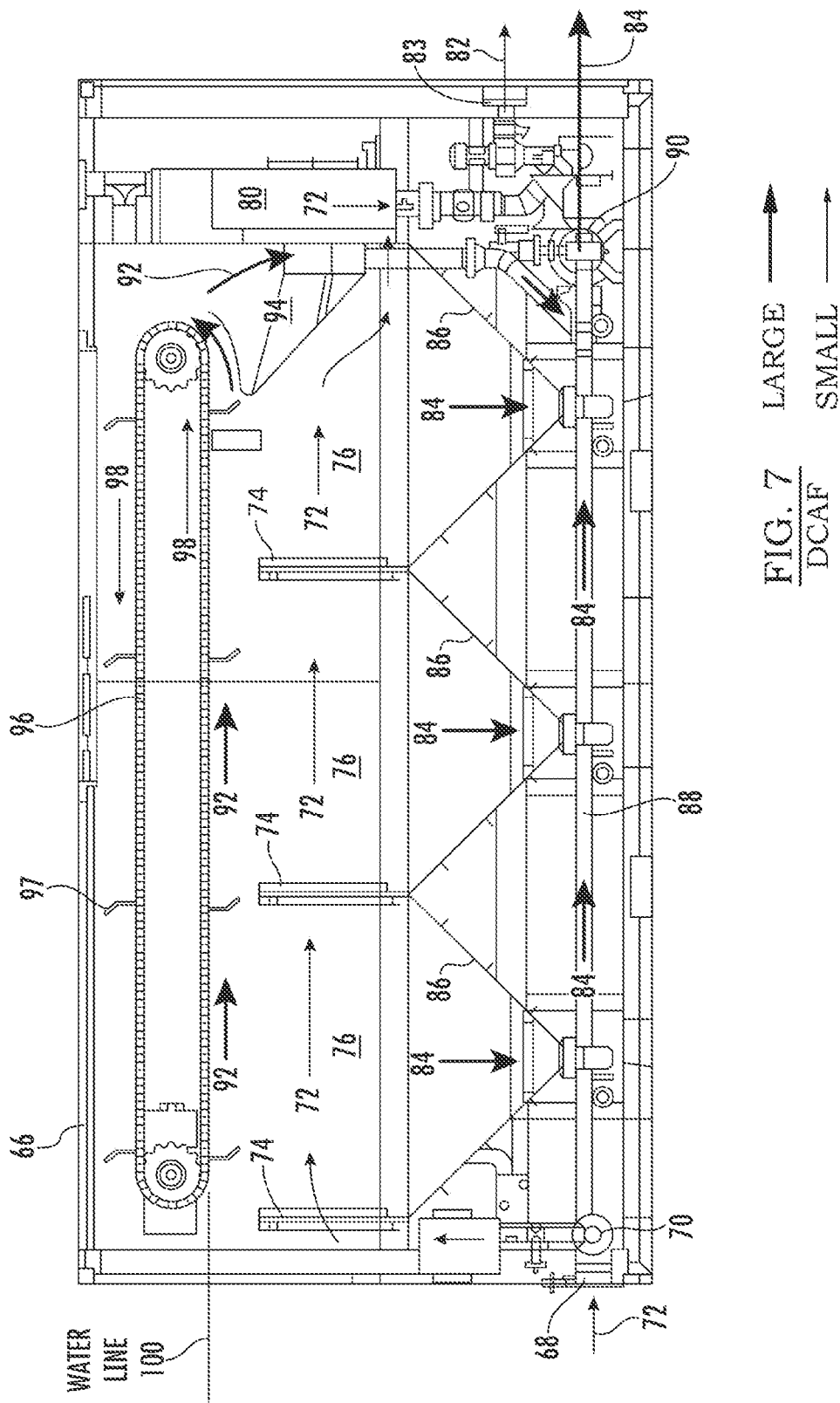
FIG. 7 is a sectional side elevational view of the third separation phase Dissolved Carbon Air Flotation (DCAF) of the anaerobic waste digestion system of FIG. 1, taken along lines 7-7 of FIG. 5.
Figure 8:
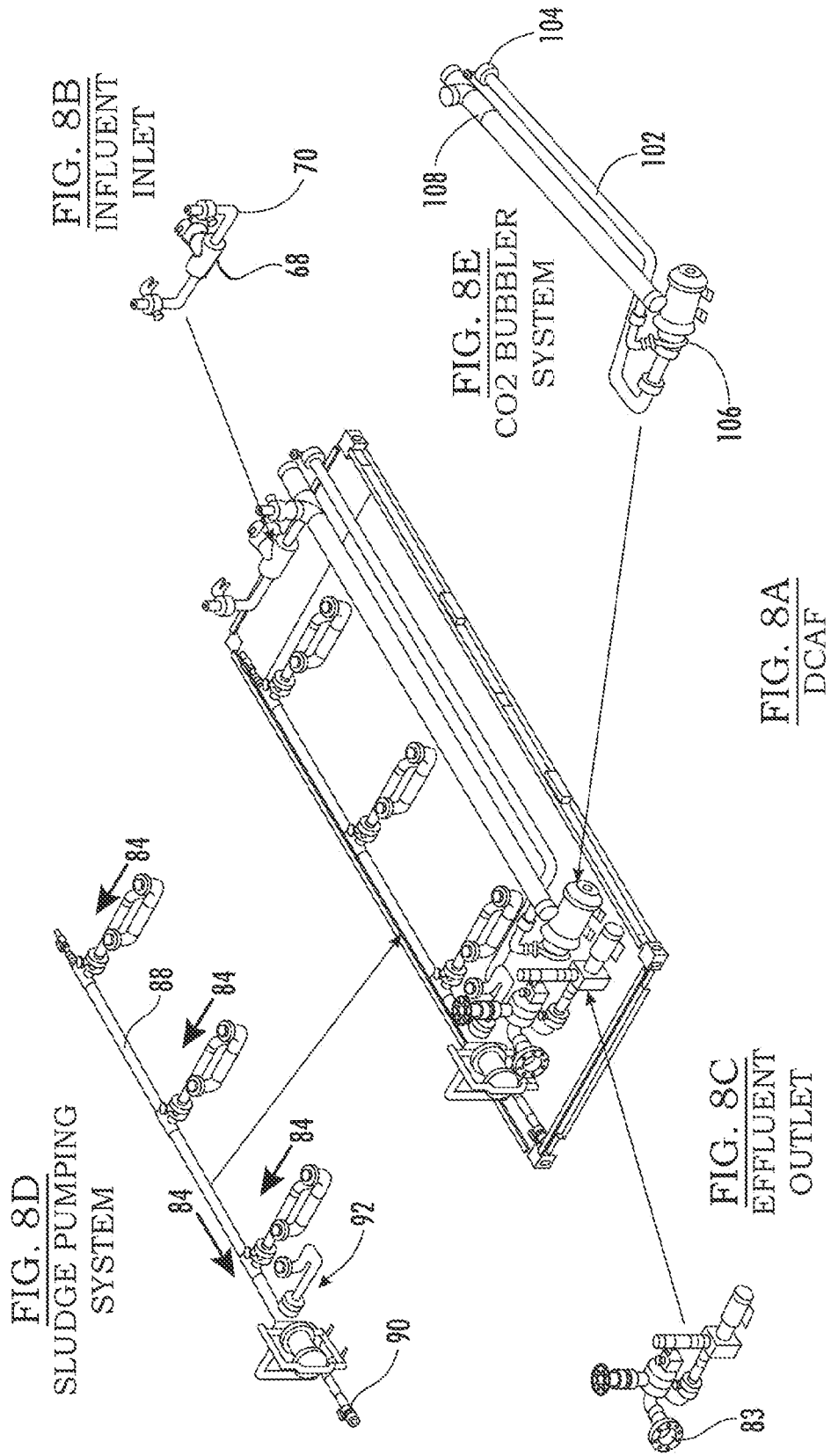
FIG. 8A is a cutaway top perspective view of the third separation phase Dissolved Carbon Air Flotation (DCAF) of the anaerobic waste digestion system of FIG. 1.
FIG. 8B is a detail perspective view of the influent inlet of the Dissolved Carbon Air Flotation (DCAF) of FIG. 8A.
FIG. 8C is a detail perspective view of the effluent outlet of the Dissolved Carbon Air Flotation (DCAF) of FIG. 8A.
FIG. 8D is a detail perspective view of the sludge pumping system of the Dissolved Carbon Air Flotation (DCAF) of FIG. 8A.
FIG. 8E is a detail perspective view of the CO2 bubbler system of the Dissolved Carbon Air Flotation (DCAF) of FIG. 8A.

As shown in FIG. 8E, a $CO_2$ bubbler system 102 provides gas to float out the large particles. $CO_2$ enters the $CO_2$ inlet 104, is pressurized by the $CO_2$ pump 106, and enters the $CO_2$ manifold 108. Fine bubbles of $CO_2$ are formed by means well known in the industry. In FIGS. 6 and 7, the $CO_2$ bubbles enter the separation zones 76, each zone capable of adjusting bubble flow, and cause the large surface area particles to float upward, forming a scum on the surface of the fluid. Heavier particles move quickly, and will drop out into the sludge hopper 86. Scum flow 92 is skimmed by conveyor blades 97 of the conveyor 96, and flow in the conveyor direction 98 into the scum hopper 94. The scum flow 92 moves downward into the sludge manifold 88 to mix with the sludge flow 84. The mixed heavy solids are returned to the screen separators 38 for further processing, or sent to screen 42 and collected in tank 44 as High P solids.

Turning now to FIGS. 9-18, as well as FIGS. 1-3, the fourth phase 110 of the Anaerobic Waste Digestion System 20 is gas production. The present disclosure utilizes a gas producer 110, including a Low Solids Anaerobic Digester, or LSAD, of a horizontal flow design. By contrast, the typical prior art design is vertical flow. The horizontal flow configuration reduces installation cost by working at one level. Operating cost is thus reduced by not pumping viscous fluids upward to process equipment. Thermal losses are minimized by installation below ground, wherein soil serves as insulation. The horizontal configuration permits the simultaneous controlling of Solids Retention Time (SRT) and recirculation.

Figure 9:
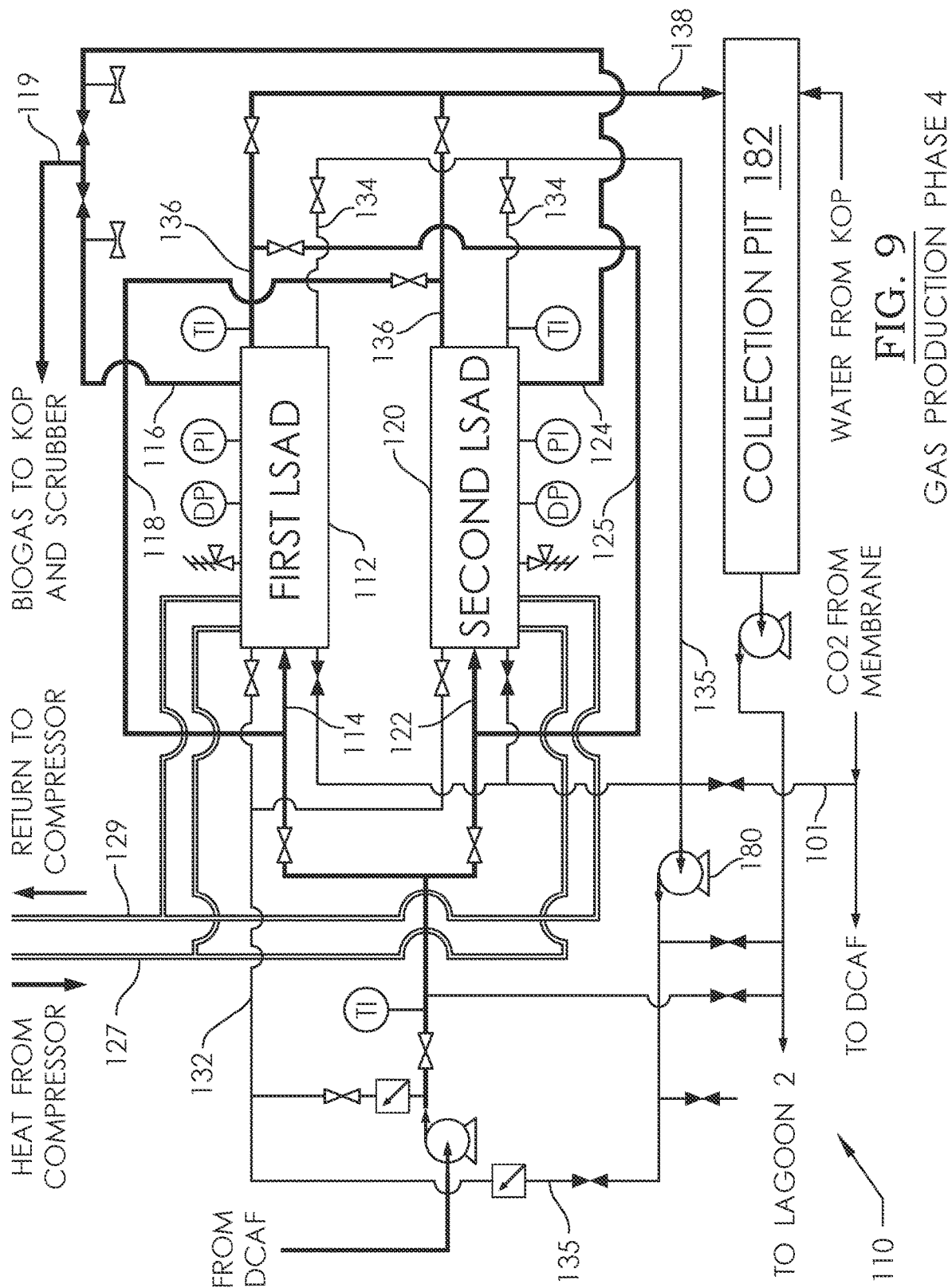
FIG. 9 is an enlarged detail schematic diagram of the gas production fourth phase of the anaerobic waste digestion system of FIG. 1.
Figure 10:
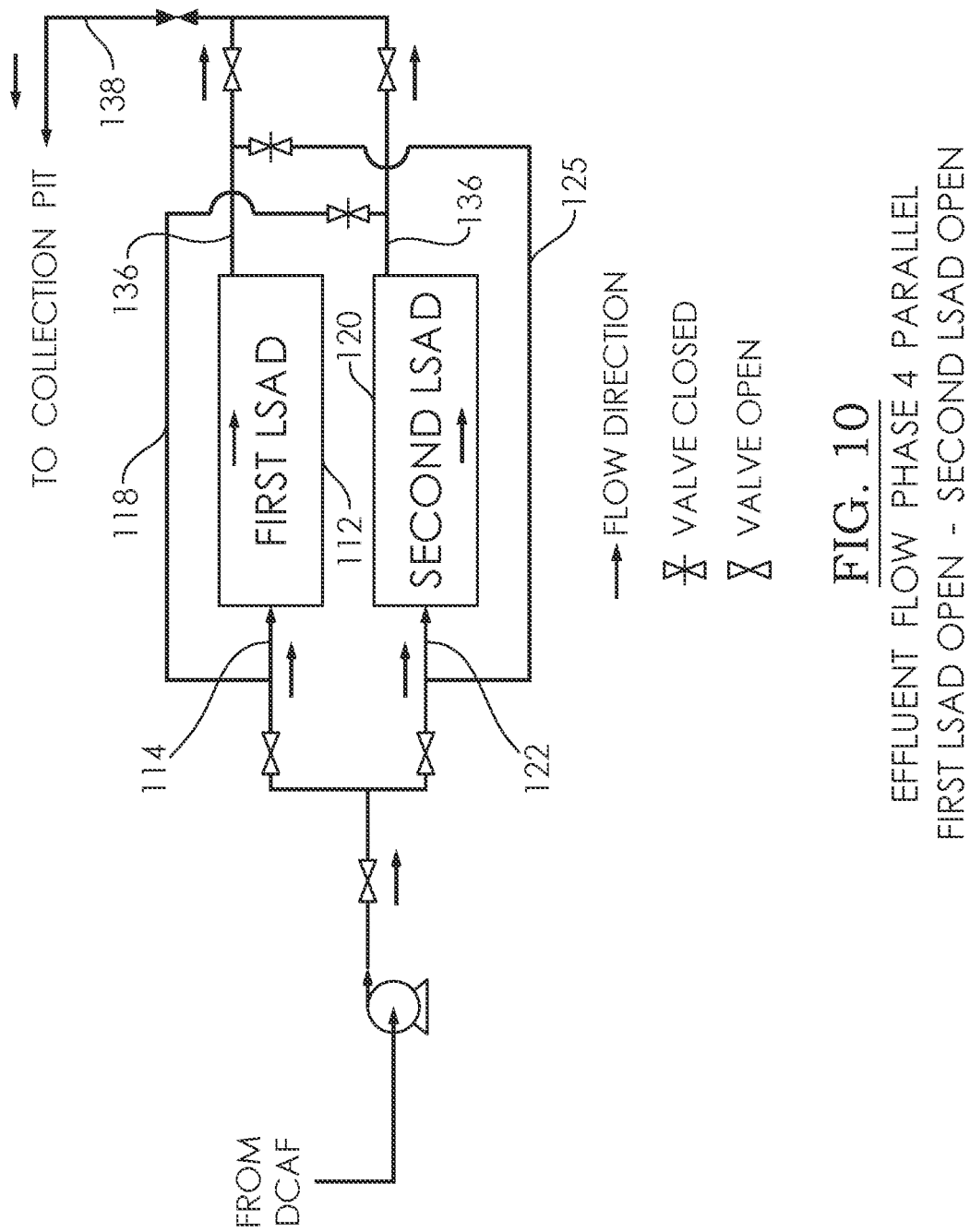
FIG. 10 is an enlarged detail schematic diagram of the gas production fourth phase of the anaerobic waste digestion system of FIG. 1, showing parallel flow through the first cell and the second cell.

As shown in FIG. 9, two digesters are provided, LSAD first cell 112, and LSAD second cell 120. The two cell LSAD design allows operation in a variety of flow configurations. FIG. 10 shows a parallel flow setup wherein feedstock flows through each cell at about the same rate. Feedstock influent enters LSAD first cell 112 at inlet 114. Biogas leaves LSAD first cell 112 at outlet 116. A bypass 118 is provided for changing flow. Similarly, feedstock influent enters LSAD second cell 120 at inlet 122. Biogas leaves LSAD second cell 120 at outlet 124. A bypass 125 is provided for changing flow. The parallel flow setup will maximize the flow rate through the gas production fourth phase 110. As the biogas 119 is generated, it exits LSAD first cell biogas outlet 116 and LSAD second cell biogas outlet 124. The biogas 119 travels downstream for refinement. Additional $CO_2$ is added into the recirculation line 101 to enhance methane generation. This $CO_2$ is dissolved in the LSAD effluent flow 138, which exits the LSAD effluent outlet 136 and is conveyed to the collection pit 182. Thus, the load on the gas upgrade system downstream is reduced, further limiting greenhouse gas emissions. Solubilized $CO_2$ can be used to produce food-grade $CO_2$ and sold, or to grow algae and duckweed for co-digestion or feed supplement.

Figure 11:
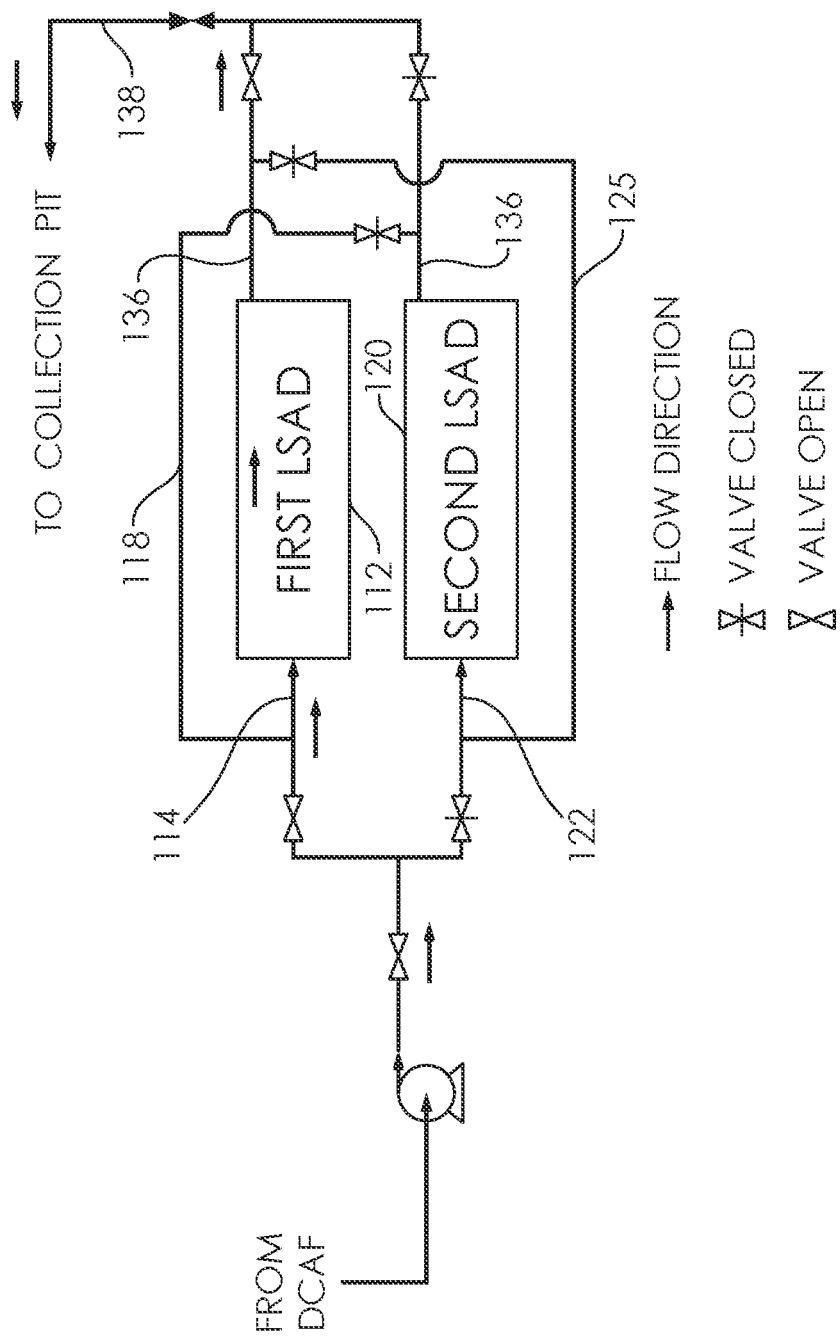
FIG. 11 is an enlarged detail schematic diagram of the gas production fourth phase of the anaerobic waste digestion system of FIG. 1, showing maintenance with the first cell open and the second cell closed.

FIG. 11 shows a maintenance setup wherein feedstock flows through only one cell, while the other cell is cleaned and repaired. Feedstock influent enters LSAD first cell 112 at inlet 114. Effluent leaves LSAD first cell 112 at outlet 136. The bypass 118 is not used. Feedstock influent is blocked from entering LSAD second cell 120 at inlet 122. Effluent from LSAD first cell outlet 136 is blocked from entering LSAD second cell at inlet 122. The bypass 125 is not used. The maintenance setup allows the gas production to proceed at a reduced rate during work on LSAD second cell.

Figure 12:
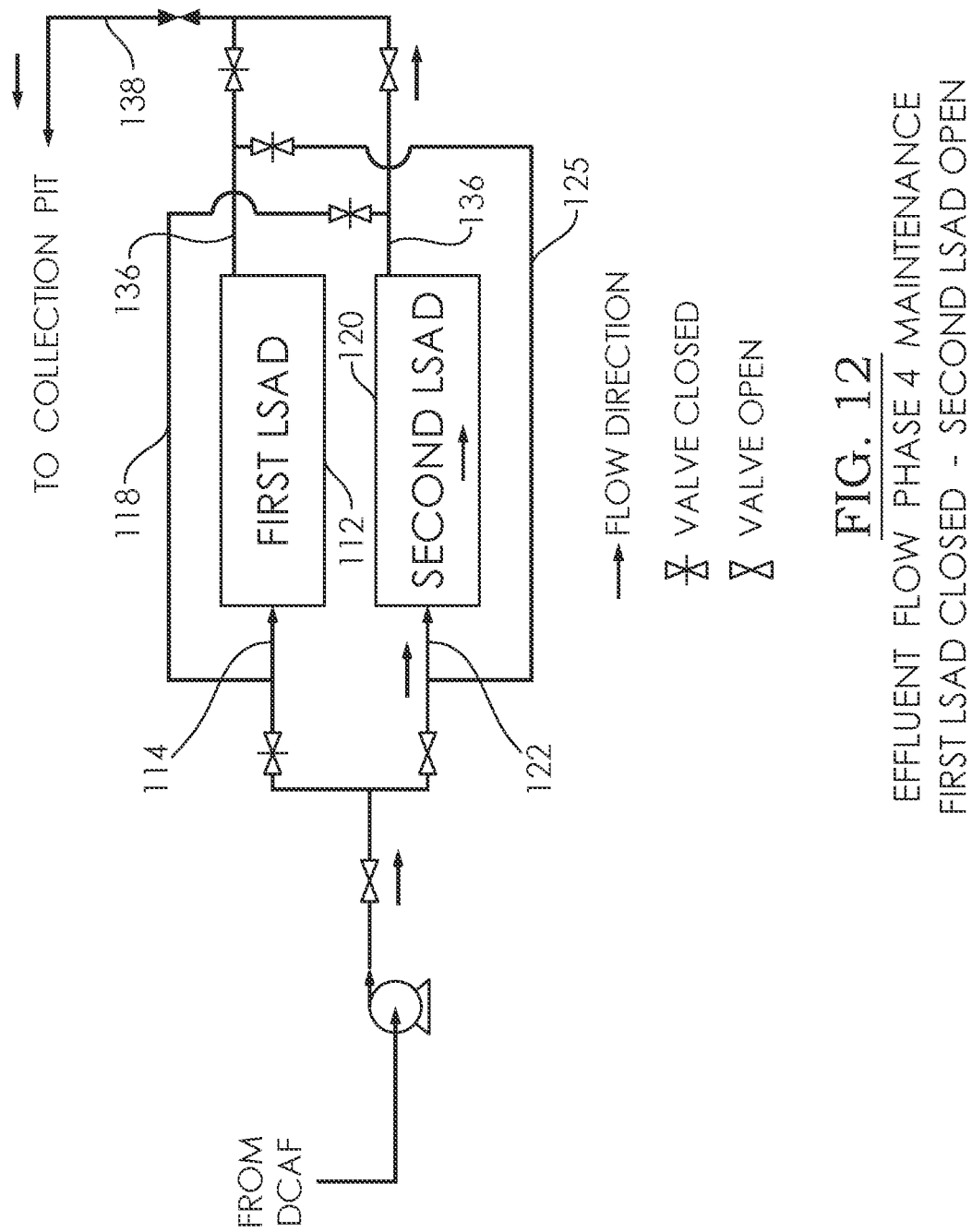
FIG. 12 is an enlarged detail schematic diagram of the gas production fourth phase of the anaerobic waste digestion system of FIG. 1, showing maintenance with the first cell closed and the second cell open.

FIG. 12 shows a maintenance setup wherein feedstock flows through only one cell, while the other cell is cleaned and repaired. Feedstock influent enters LSAD second cell 120 at inlet 122. Effluent leaves LSAD second cell 120 at outlet 136. The bypass 125 is not used. Feedstock influent is blocked from entering LSAD first cell 112 at inlet 114. Effluent from LSAD second cell outlet 136 is blocked from entering LSAD first cell at inlet 114. The bypass 118 is not used. The maintenance setup allows the gas production to proceed at a reduced rate during work on LSAD first cell.

Figure 13:
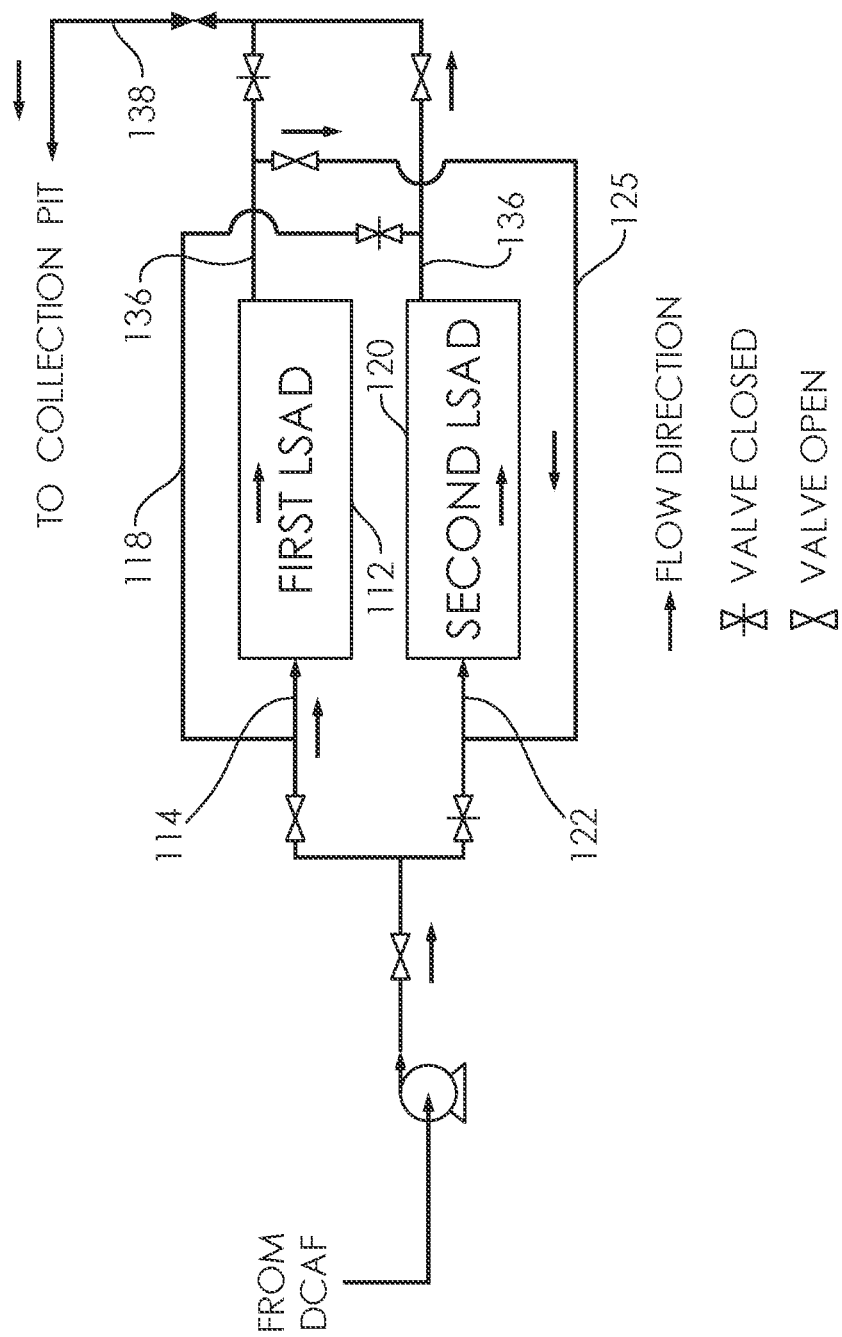
FIG. 13 is an enlarged detail schematic diagram of the gas production fourth phase of the anaerobic waste digestion system of FIG. 1, showing two-phase series flow firstly through the first cell and secondly through the second cell.

FIG. 13 shows a series flow setup wherein feedstock flows first through one cell, then through the other cell. Feedstock influent enters LSAD first cell 112 at inlet 114. Effluent leaves LSAD first cell 112 at outlet 136, and is blocked from passage downstream. The bypass 118 is not used. Effluent flows through bypass 125 to LSAD second cell at inlet 122. Effluent leaves LSAD second cell 120 at outlet 136 to flow downstream. The series flow setup allows the gas production to proceed as a dual, or two phase digester, allowing optimal individual environments for acid forming bacteria in one cell, and methane-forming bacteria in the other cell.

Figure 14:
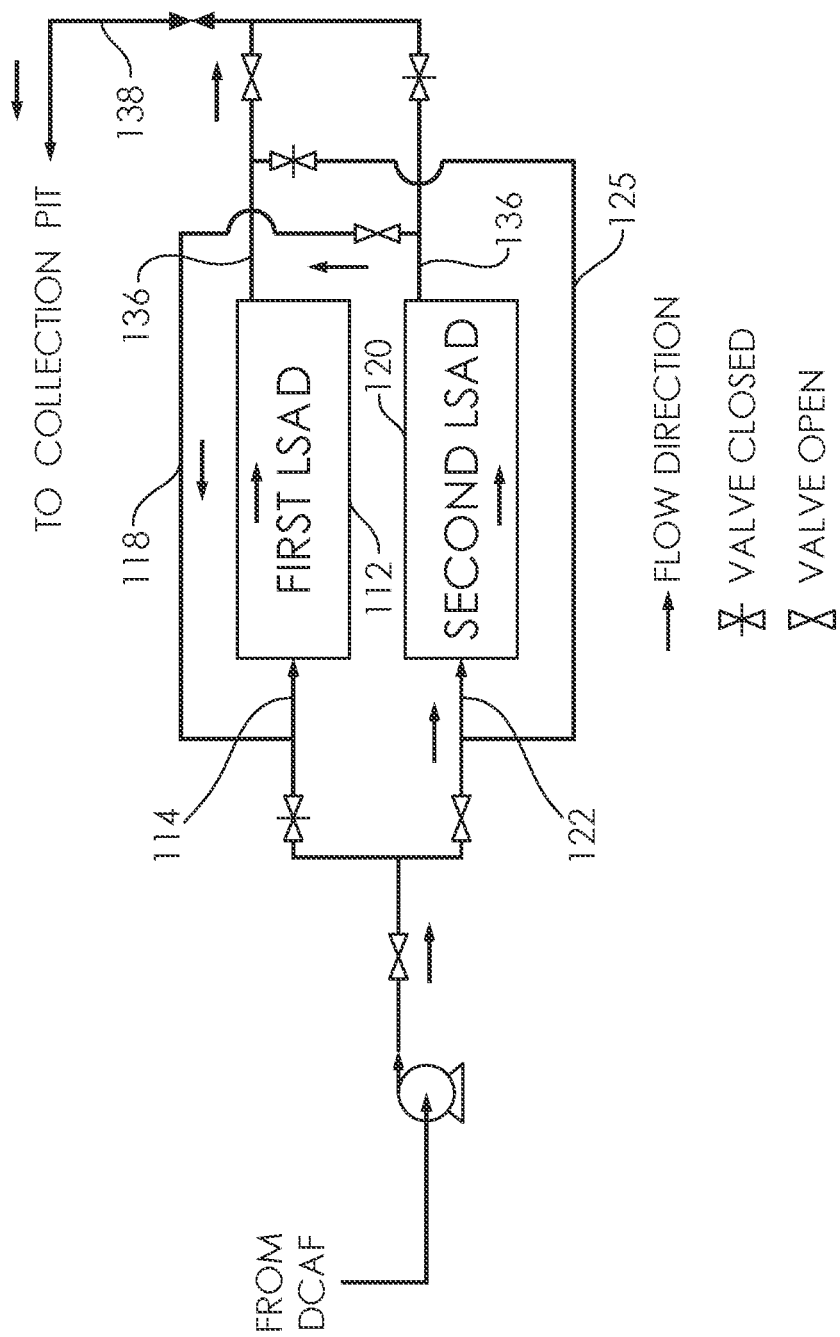
FIG. 14 is an enlarged detail schematic diagram of the gas production fourth phase of the anaerobic waste digestion system of FIG. 1, showing two-phase series flow firstly through the second cell and secondly through the first cell.

FIG. 14 shows another series flow setup. Feedstock influent enters LSAD second cell 120 at inlet 122. Effluent leaves LSAD second cell 120 at outlet 136, and is blocked from passage downstream. The bypass 125 is not used. Effluent flows through bypass 118 to LSAD first cell at inlet 114. Effluent leaves LSAD first cell 112 at outlet 136 to flow downstream. The series flow setup allows the gas production to proceed as a dual, or two phase digester.

In the fourth phase 110, methane is continuously generated by the interaction of volatile solids and specialized bacteria in enclosed warm containers operating at approximately 68-140° F., without the presence of oxygen. The present disclosure operates in the Mesophilic range of approximately 68-112° F. The heat can be supplied by any source, within the system or external to the system. Preferably, the heat is supplied by the compressor waste heat of compression, and this is understood to be non-limiting. In FIGS. 15-18, a heat-exchange fluid, typically glycol-based, transfers heat from the compressor 202 to the influent flow 140 of the LSAD 112, 120, by heat supply conduit 127 connected to the heat supply fluid manifold 128. Heat transfers from heat-exchange fluid flow 126 to the LSAD influent flow 140 by means of a fluid tubing heat exchanger 131. Heat-exchange fluid flow 126 exits the LSAD by the heat return fluid manifold 130, and is returned to the compressor 202 by heat return conduit 129. By recovering waste heat from the compressor 202, a reduced amount of product biogas is used for heating the digester. System efficiency and methane production is thereby optimized.

A common prior-art digester design, Plug Flow, works on a simple process wherein raw manure is continuously fed into a heated anaerobic flow-through chamber. Bacteria is held in suspension within the solids themselves. Typically, de-bulked solids, effluent, and methane are discharged 3 weeks later. Published conversion efficiency (breaking down COD) of dairy effluent from the market-leading Plug Flow manufacturer is under 10%. In the case of other prior-art digester designs, such as Continuously Stirred and Lagoon, bacteria is free-floating in the feedstock. Mixing the organic particles with the bacteria is done through mechanical stirring or turning over the solids. The bacteria continually washes out, and must be replenished. In all prior-art designs, settled solids require cleaning out periodically, or efficiency will drop and the system will fail.

In the present disclosure Fixed Film LSAD design, instead of the bacteria residing in the moving solids or effluent, the LSAD system places the bacteria on permanent structures. Once the bacteria is introduced, it is Fixed, or permanently resides in the digester. The Film is the adhesive coating generated by the bacteria that confines them to the digester. In the LSAD, the film and bacteria reside in a heated water environment devoid of oxygen. The bacteria grow on rigid vertical walls that permit them to consume organic particles floating by, reproduce, and grow in quantity and size. This configuration precludes large particles blocking digestion of small particles, as seen in prior-art digesters. The length of time it takes for effluent to completely flow through the digester is the Hydraulic Residence Time (HRT). Prior-art digesters have an HRT of up to 3 weeks. The present disclosure LSAD interaction time is about 3 days. The Solids Residence Time (SRT) can be varied, and is determined by monitoring the COD destruction seen in the recirculation of settled solids, as described hereinbelow. The SRT permits retreatment of settled solids, thereby freeing up more COD. Hydraulic Retention Time is also about 3 days. The LSAD converts useful organics to methane approximately seven times faster than prior-art systems. The published efficiency of Fixed Film digesters ranges from 60%-90%.

The LSAD cells 112, 120, are contained within digester tanks 142 constructed of R32 insulated concrete. The cells are covered with a double HDPE cover 144 that provides an insulating air layer, so as to maintain a constant system temperature. All LSAD structure and components are removable, allowing easy installation and maintenance. Cell digester tanks of the present disclosure are each 30 feet wide by 125 feet long, but these dimensions can vary, and are non-limiting. Each digester tank has first 146 and second 148 opposed sidewalls extending from an inlet endwall 150 to an outlet endwall 152. Each digester tank includes a bottom 154 extending between the first 146 and second 148 sidewalls, and extending between the inlet 150 and outlet 152 endwalls. The bottom 154 slopes downward from adjacent the first sidewall 146 to adjacent the second sidewall 148.

Figure 15:
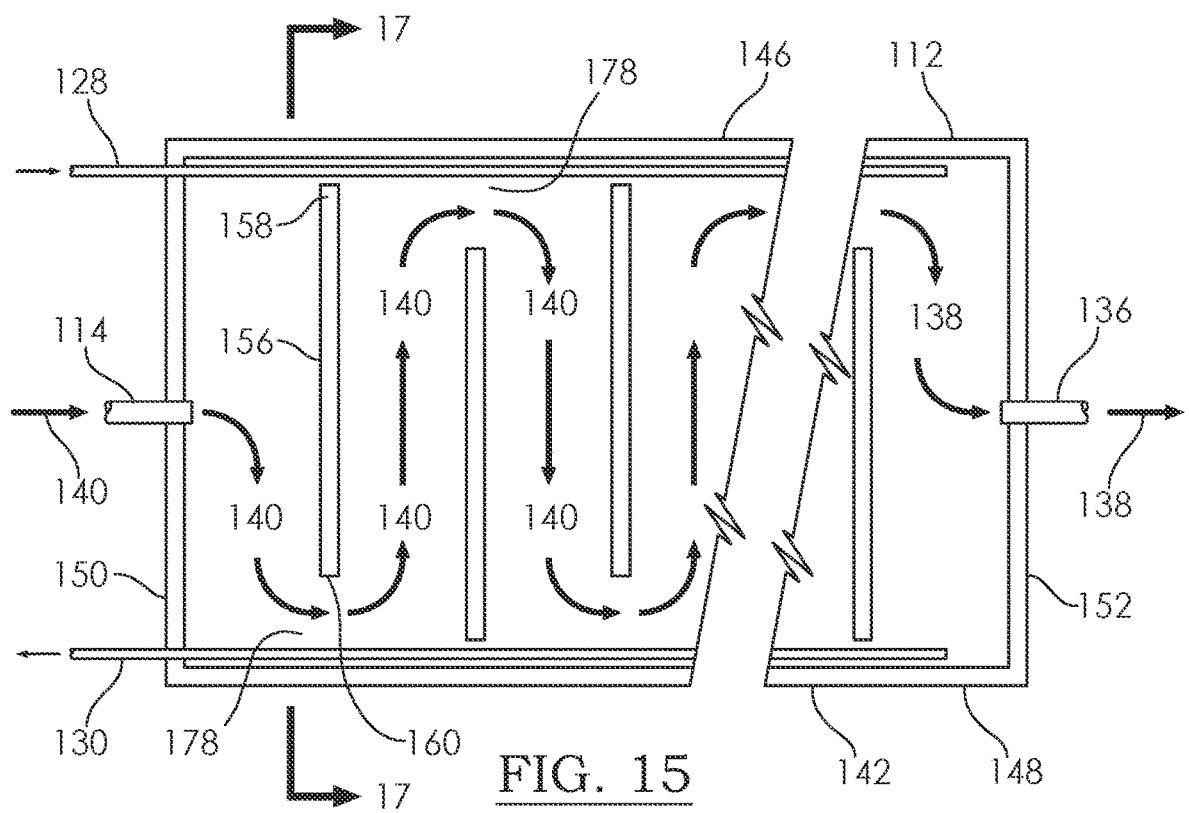
FIG. 15 is a top plan, cross-sectional view of the gas production fourth phase of the anaerobic waste digestion system of FIG. 1, taken along lines 15-15 of FIG. 17.

Biocurtains 156 are the rigid vertical walls installed inside the LSAD to provide the environment for anaerobic bacterial growth. In FIG. 15, A plurality of biocurtains 156 are spaced apart from the inlet endwall 150 to the outlet endwall 152. Every other biocurtain 156 extends from a proximal end 158 adjacent the first sidewall 146 to a distal end 160 adjacent the second sidewall 148 and spaced apart from the second sidewall 148 by a predetermined flow space 178. Each remaining biocurtain 156 extends from a proximal end 158 adjacent the second sidewall 148 to a distal end 160 adjacent the first sidewall 146 and spaced apart from the first sidewall 146 by the flow space 178. Each biocurtain flow space 178 adjacent the distal end extends from the tank bottom 154 to the wastewater surface 164. The biocurtains 156 and spaces 178 alternate so as to provide a convoluted, preferably serpentine flow of wastewater feedstock 140 through the LSAD digesters 112, 120, as shown in FIG. 15. The flow of wastewater feedstock 140 through the digester 112, 120, and around the biocurtains 156 can assume any path or flow pattern, and the path is non-limiting.

Figure 18:
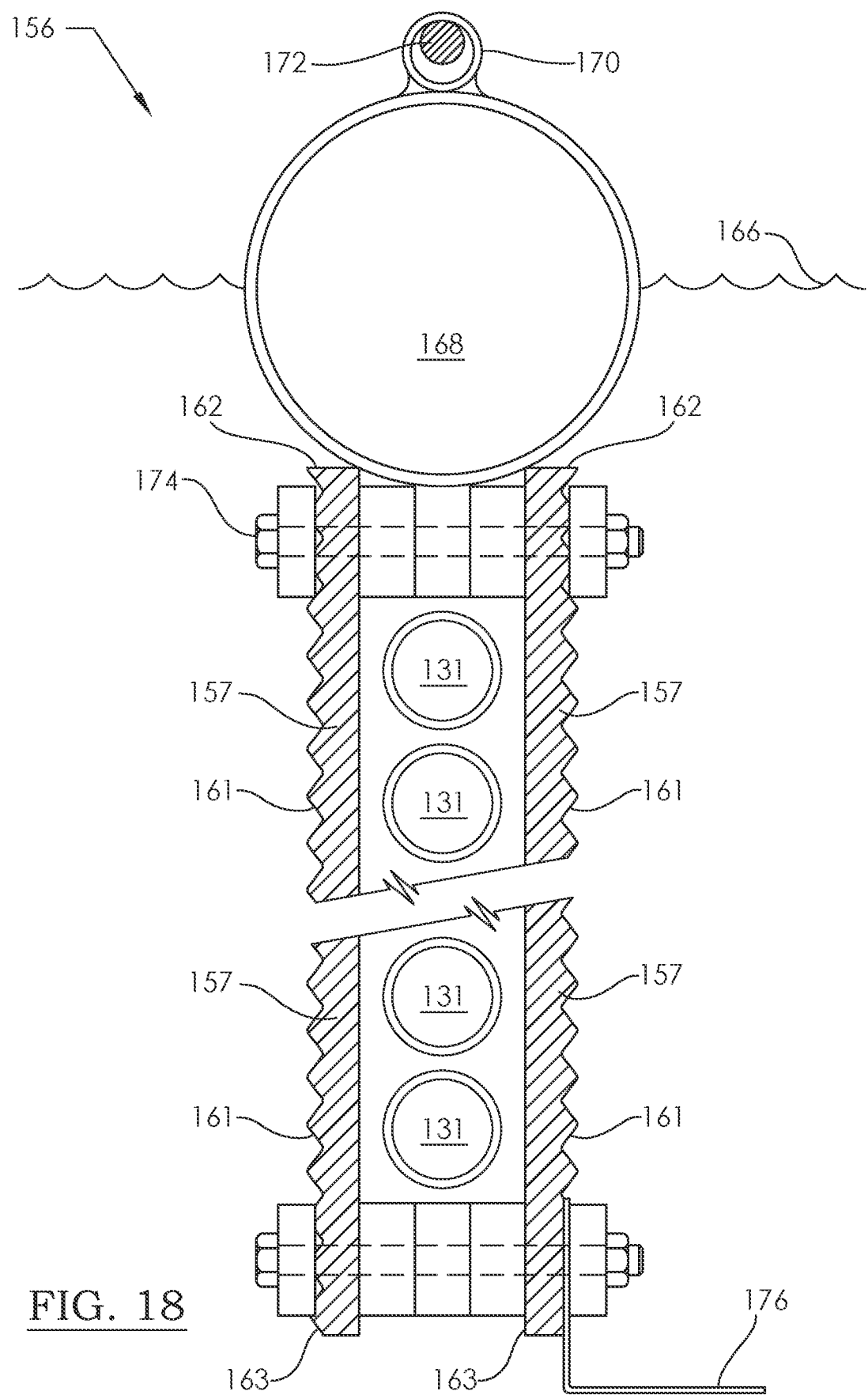
FIG. 18 is a side elevational, cross-sectional view of the biocurtain of the gas production fourth phase of the anaerobic waste digestion system of FIG. 1, taken along lines 18-18 of FIG. 17.

In FIG. 18, each biocurtain 156 has two sheets 157 of polymeric material spaced apart a predetermined distance. The biocurtain sheet material is selected from a polymeric resin such as polyethylene, polypropylene, or PET. These materials are examples, and are understood to be non-limiting. Prior-art sheet material is typically smooth. By contrast, the present disclosure sheet material has alternating ridges 161 and furrows providing a patterned or convoluted surface, so as to increase the surface area for bacterial growth. The ridges 161 are of a predetermined, maximum ridge height so as to not occlude the release of biogas excreted by the bacteria residing on the surface.

The sheets are attached to a float pipe 168, and depend downward from the float pipe 168. The float pipe 168 floats upon the surface 166 of the wastewater feedstock to support the biocurtain 156. A hanger pipe 170 is co-extensive with the float pipe 168. The hanger pipe 170 is unitary with the float pipe 168 on an upper surface thereof. An anchor cable 172 is received in the hanger pipe 170. The opposite ends of each anchor cable 172 are secured in pockets spaced apart along upper edges of the sidewalls, to anchor the biocurtains. Each biocurtain sheet 157 extends from an upper edge 162 attached by fasteners 174 to the float pipe 168, downward to a lower edge 163 anchored to the tank bottom 154 by a floor bracket 176.

Figure 17:
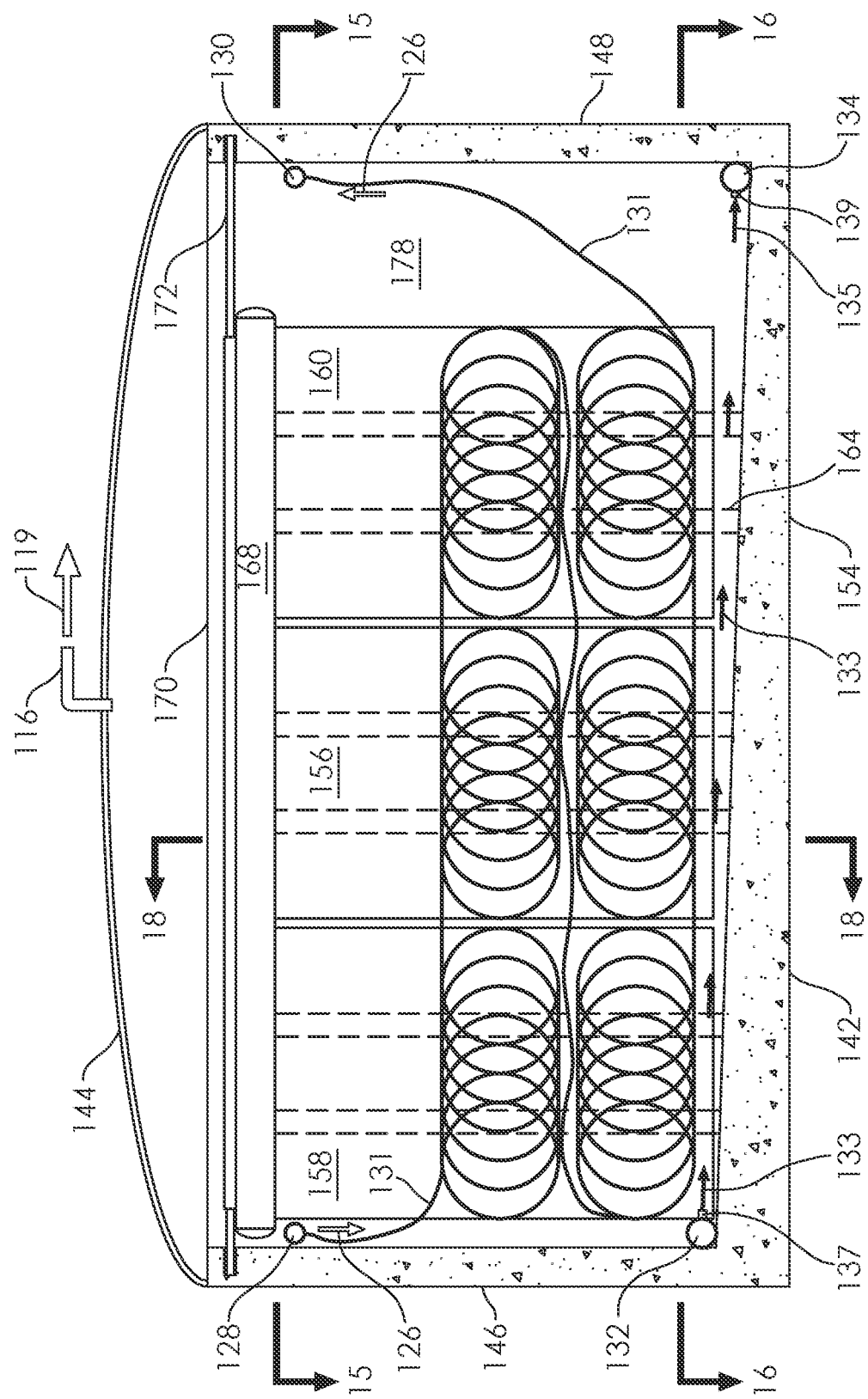
FIG. 17 is a front elevational, cross-sectional view of the gas production fourth phase of the anaerobic waste digestion system of FIG. 1, taken along lines 17-17 of FIG. 15.

The LSAD biocurtains 156 include heat exchangers. Sandwiched between the two sheets 157 of polymeric material is polymeric fluid tubing heat exchanger 131, containing the glycol heat exchange fluid 126, shown in FIG. 18. The heat exchange glycol fluid absorbs waste heat from the compressor 202. The glycol fluid enters the LSAD through a heat supply fluid manifold 128. Heat-exchange fluid flow 126 is shown in FIG. 17. From the manifold 128, fluid tubing 131 carries the waste heat to the biocurtain 156 where the heat is released to the biocurtain sheet 157, so as to maintain the bacteria at an optimum temperature. The fluid tubing 131 can assume a variety of flow field patterns commonly used in heat exchangers. FIG. 17 shows a flat spiral pattern, but this example is understood to be non-limiting. The glycol fluid leaves the LSAD through a heat return fluid manifold 130 to be returned to the compressor 202. Prior art digesters heat the entire volume of digester water, using product biogas, which burns a significant amount of biogas. In contrast, the present LSAD disclosure uses waste heat of compression to heat the biocurtain only, thereby providing a homeostatic environment for the bacteria all year. This saves about 10%-30% of the biogas compared to the prior art, depending upon the location of the digester and the average ambient temperature at the location.

Figure 16:
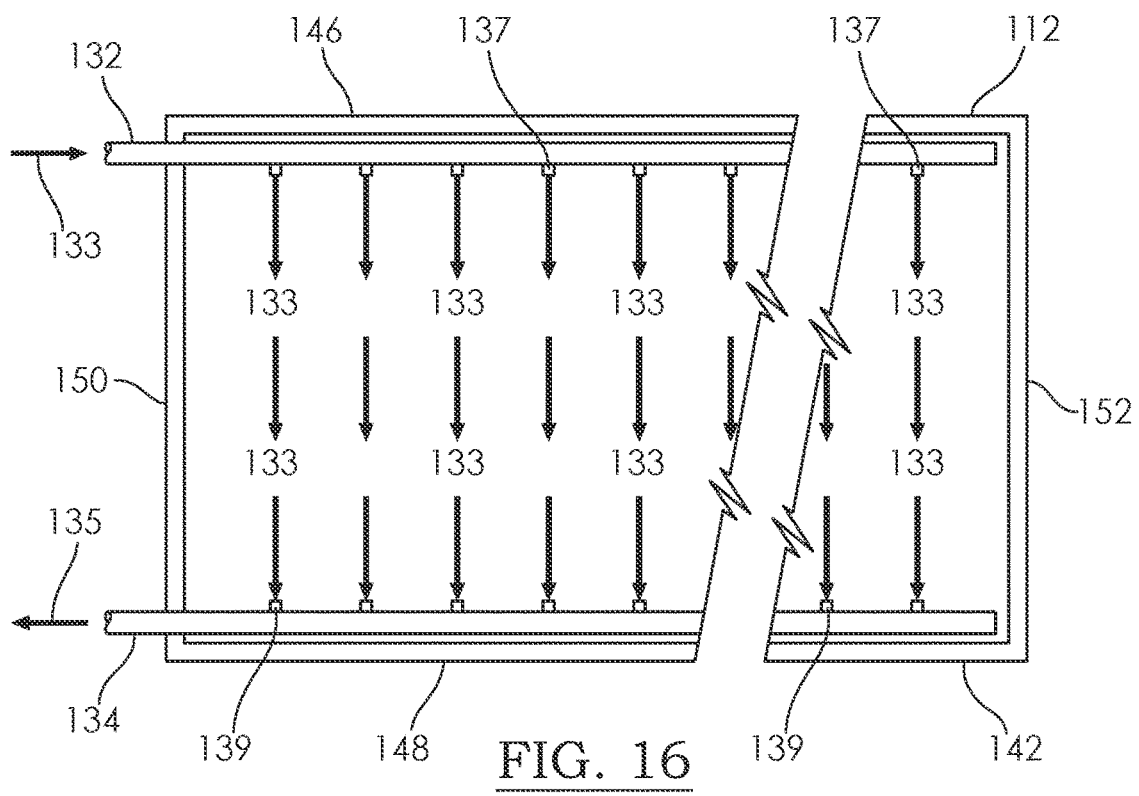
FIG. 16 is a top plan, cross-sectional view of the gas production fourth phase of the anaerobic waste digestion system of FIG. 1, taken along lines 16-16 of FIG. 17.

Prior-art Fixed Film digesters are sensitive to clogging due to excessive biofilm thickness and high suspended solids concentration in the wastewater feedstock. The present disclosure overcomes this problem in the solids separation as described above, and in the LSAD design. The rigid, vertically mounted, high surface area biocurtain 156 provides a lateral flow of the wastewater feedstock, thereby allowing lighter and smaller organics to remain in the flow stream. Thus, larger solids will settle downward to the tank bottom 154 to become settled solids. In FIGS. 16-17, some of the LSAD wastewater influent flow 140 is diverted to the sweep jet inlet manifold 132. Sweep jet nozzles 137 are arrayed along the length of the sweep jet inlet manifold 132. The sweep jet nozzles 137 direct influent across the tank bottom 154 as sweep jet flow 133. This stirs up and mixes with the settled solids, to become settled solids flow 135, which is drawn by the settled solids nozzles 139 into the settled solids outlet manifold 134. A settled solids pump 180 pulls suction on the settled solids outlet manifold 134. The settled solids particles are reduced in size by fluid shear in the settled solids pump 180. Hence, settled solids are recycled through the 3-phase separation process to increase biogas production and system process efficiency. Recirculation and comminution of settled solids provides the ability to control the Organic Loading Rate, provides pH buffering, increases hydrolization, and increases digester stability. The LSAD SRT can be varied independently, or decoupled, with respect to the HRT by means of the settled solids recirculation. The settled solids effluent flow 135 will be monitored for particle size reduction, and corresponding increases in COD. In order to maintain SRT, ORL, pH, particle size, and COD balance, a certain percentage of the settled solids effluent is discharged into second lagoon 47 as a buffer.

LSAD effluent flow 138 exits the LSAD effluent outlet 136 and is conveyed to the collection pit 182. This is wastewater with substantially no solid particulate matter. LSAD effluent flow 138 is pumped or flows by gravity to the first 46 or second 47 lagoon. Effluent is allowed to clear, and then is sent to the EQ pit 26 or the Sand Lane 28 for washdown.

Figure 19:
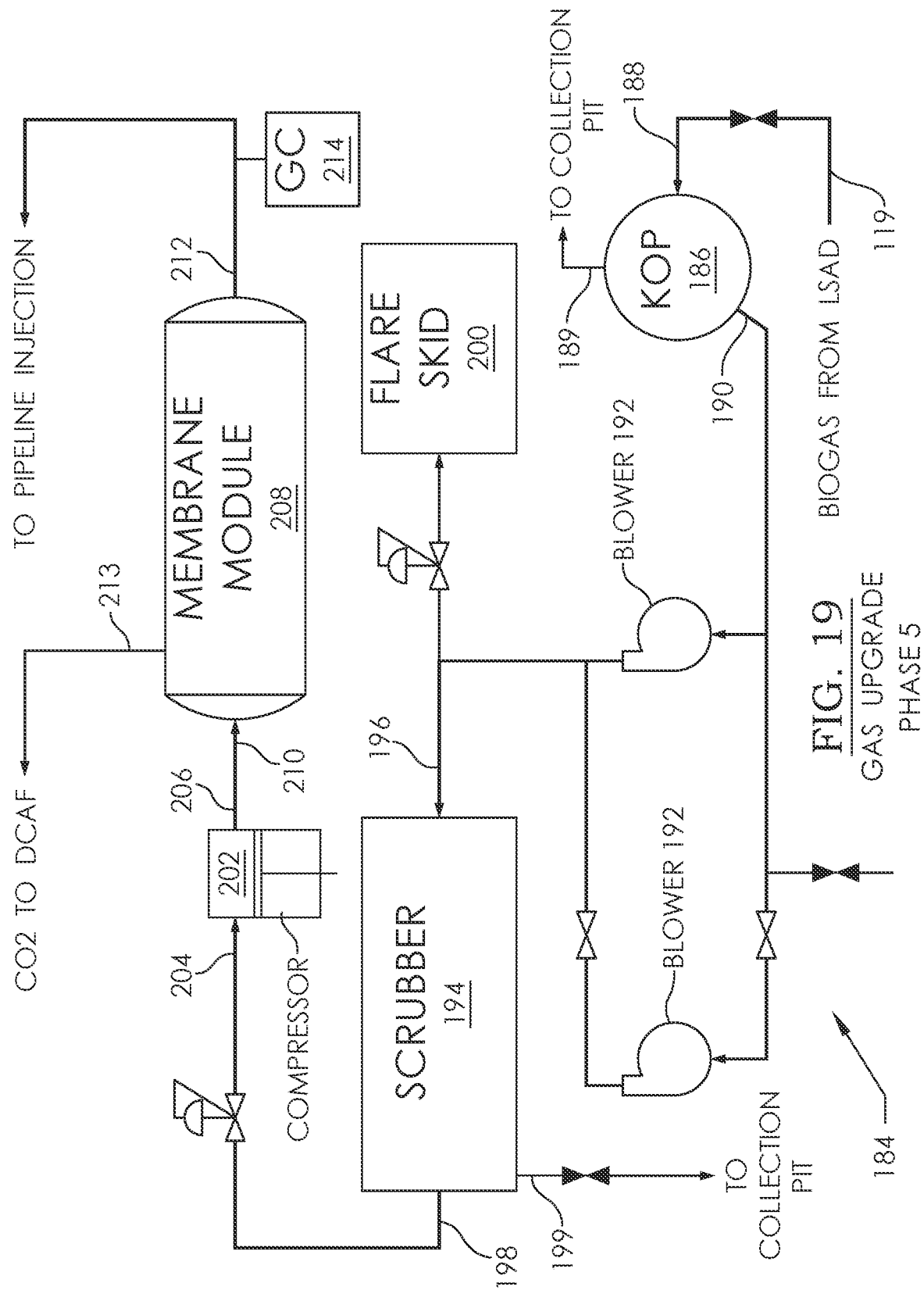
FIG. 19 is an enlarged detail schematic diagram of the gas upgrade fifth phase of the anaerobic waste digestion system of FIG. 1.

Referring now to FIG. 19, as well as FIG. 1, the fifth phase 184 of the Anaerobic Waste Digestion System 20 is gas upgrade, including a gas refiner 184. The present disclosure utilizes a Knock Out Pot (KOP) 186 downstream of the LSAD cells 112, 120. Raw methane LSAD cell biogas flow 119 exits the LSAD cell biogas outlets 116, 124, and enters the KOP 186 at the KOP inlet 188. The KOP 186 removes very fine droplets of water entrained in the gas and removes any liquid carryover in the biogas. Liquid exits the by the KOP effluent outlet 189, and is sent to the collection pit 182. Biogas leaves at the KOP gas outlet 190.

From the KOP outlet 190, raw methane biogas is sent to the scrubbing system, or scrubber 194 by means of redundant blowers 192. The scrubber 194 is a 3 phase separator. The scrubber 194 removes water vapor, particulate matter, and contaminant gas from the biogas. The scrubber 194 typically is a commercially available product such as the Series 77V Coalescing Filter, manufactured by PECOFacet. The scrubber 194 may include an activated charcoal trap. Depending upon the site, another scrubber may be included, such as an Iron Sponge for Hydrogen Sulfide (H2S) control. Methane enters the scrubber gas inlet 196 and clean gas exits the scrubber gas outlet 198. The coalesced liquid drains through the scrubber effluent outlet 199 to the collection pit 182. Excess gas, or excess pressure in the LSAD 112 or 120 can be rerouted and burned off by the flare skid 200.

The methane gas is compressed by a commercially available compressor 202. The methane enters the compressor inlet 204, and exits the compressor outlet 206. The methane gas then enters a membrane module 208 at membrane module inlet 210. The membrane technology purifies natural gas by removing gas and liquid impurities. Carbon dioxide is removed and sent upstream to the DCAF CO2 bubbler system 102, and the recirculation line 101, as described above. Since the CO2 gas will be pumped into the DCAF 66 under pressure, a high percentage of the gas will dissolve. Optionally, some of the CO2 tail gas from the membrane module 208 can be sent to the second lagoon 47, to be dissolved into the wastewater. The methane gas exits the membrane module 208 at membrane module outlet 212. The methane quality is measured by a gas chromatograph 214, so as to ensure consistency of the final gas composition.

The Anaerobic Waste Digestion System 20 is monitored and controlled by a process control 220. The process control 220 includes a central processor, a memory, and input and output connections. Input signals are received from instruments throughout the system. Input signals comprise pH, temperature, pressure, COD, and mass flow at various critical points of the system. Input signals further comprise closed contacts, electrical voltage and current. Output signals are sent to pressure control valves, temperature control valves, and emergency shutdown systems. A flare skid 200 and automatic shutoff valves are installed for safety. Control Logic is programmed to monitor the entire process and is able to provide operator ease of use and real time process status updates.

Figure 20:
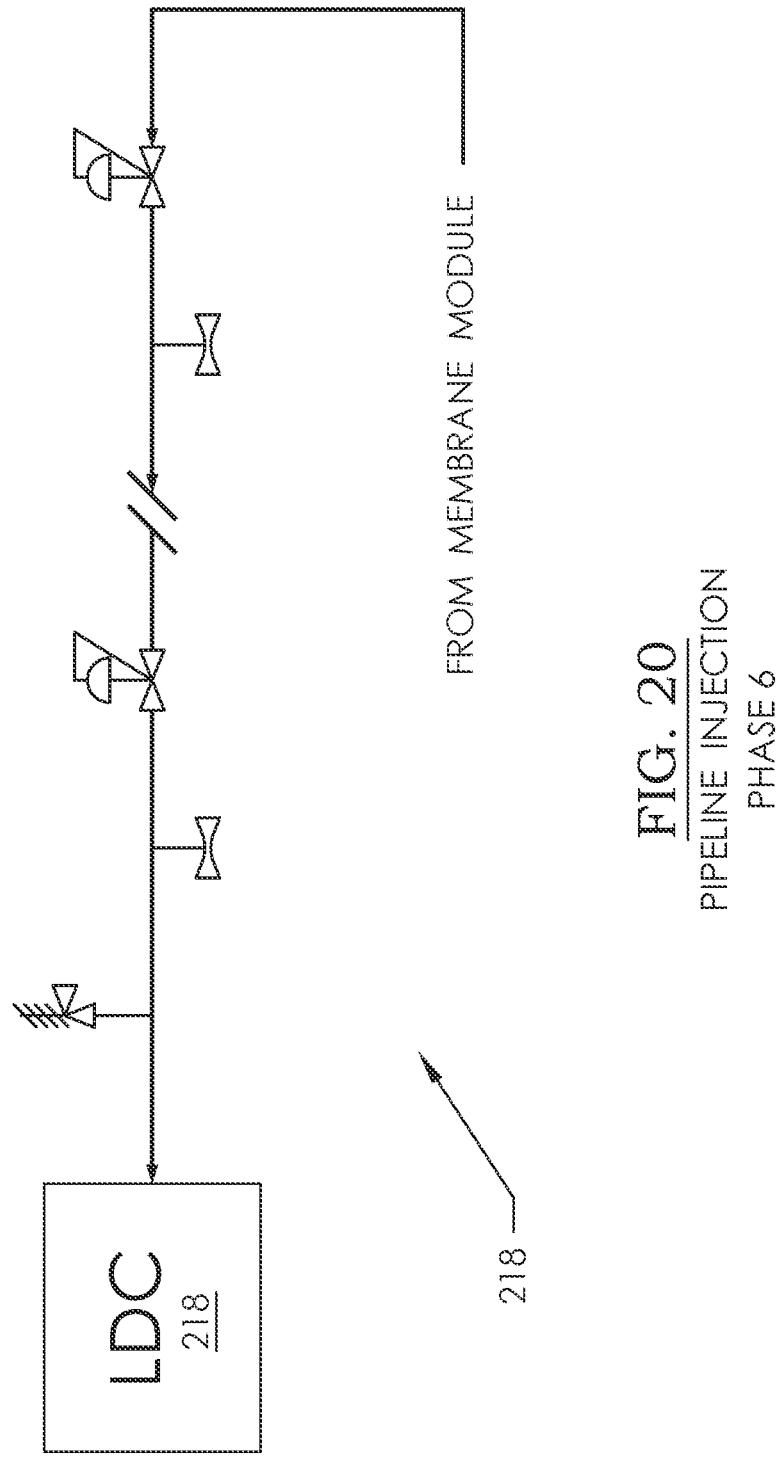
FIG. 20 is an enlarged detail schematic diagram of the pipeline injection sixth phase of the anaerobic waste digestion system of FIG. 1.
Figure 21:
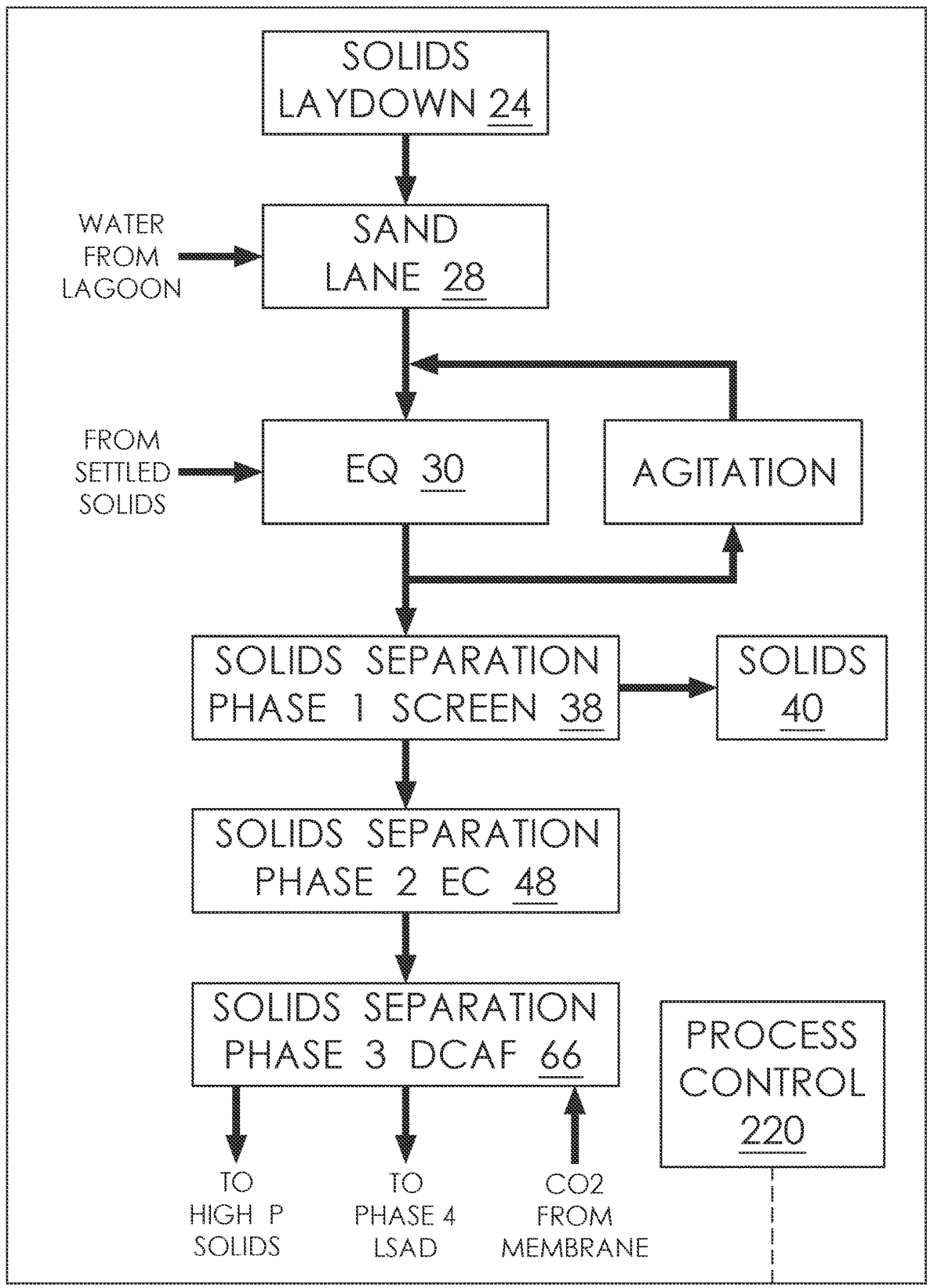
FIG. 21 is a block diagram of the anaerobic waste digestion system of FIG. 1.
Figure 22:
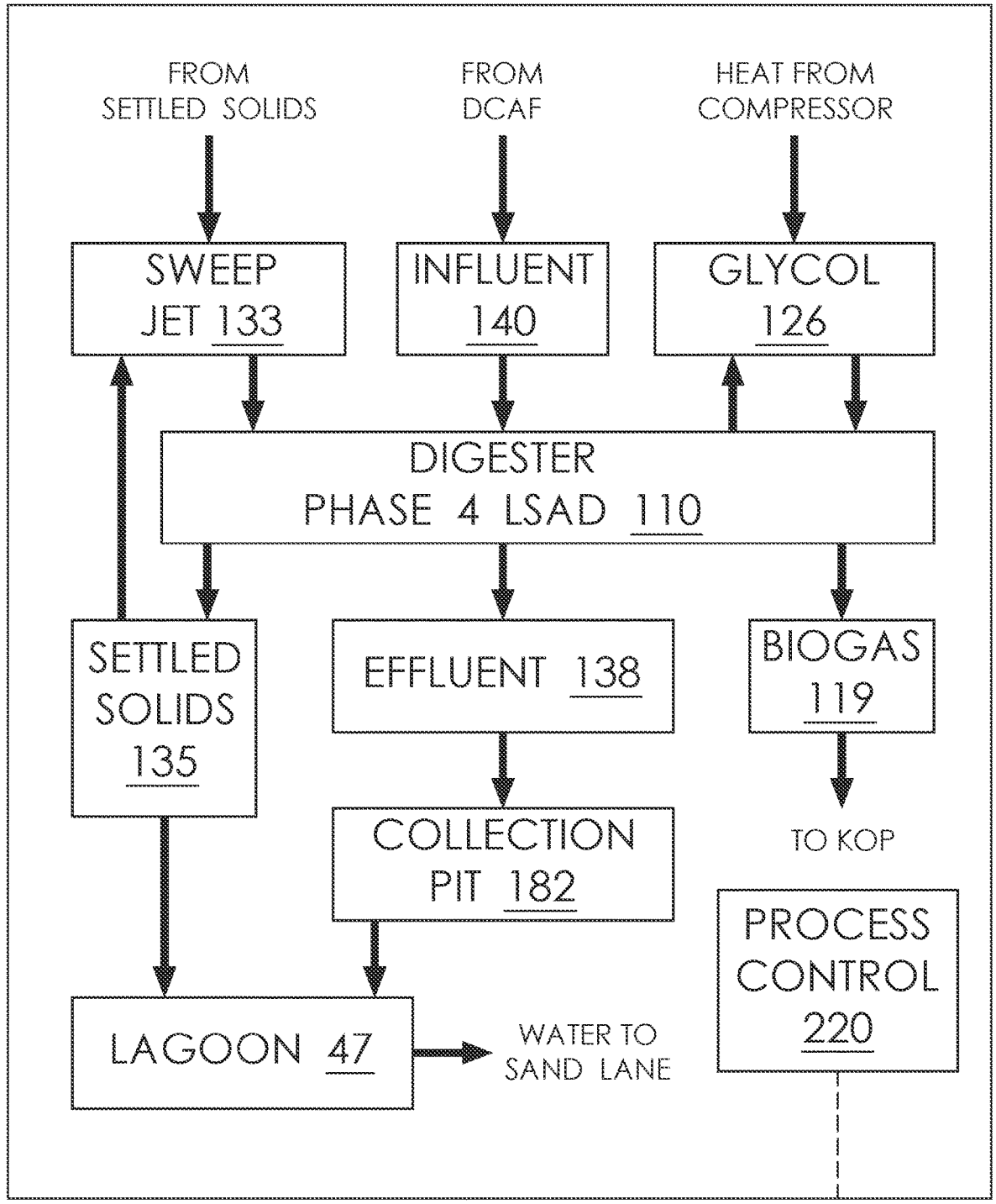
FIG. 22 is a block diagram of the anaerobic waste digestion system of FIG. 1, continued from FIG. 21.
Figure 23:
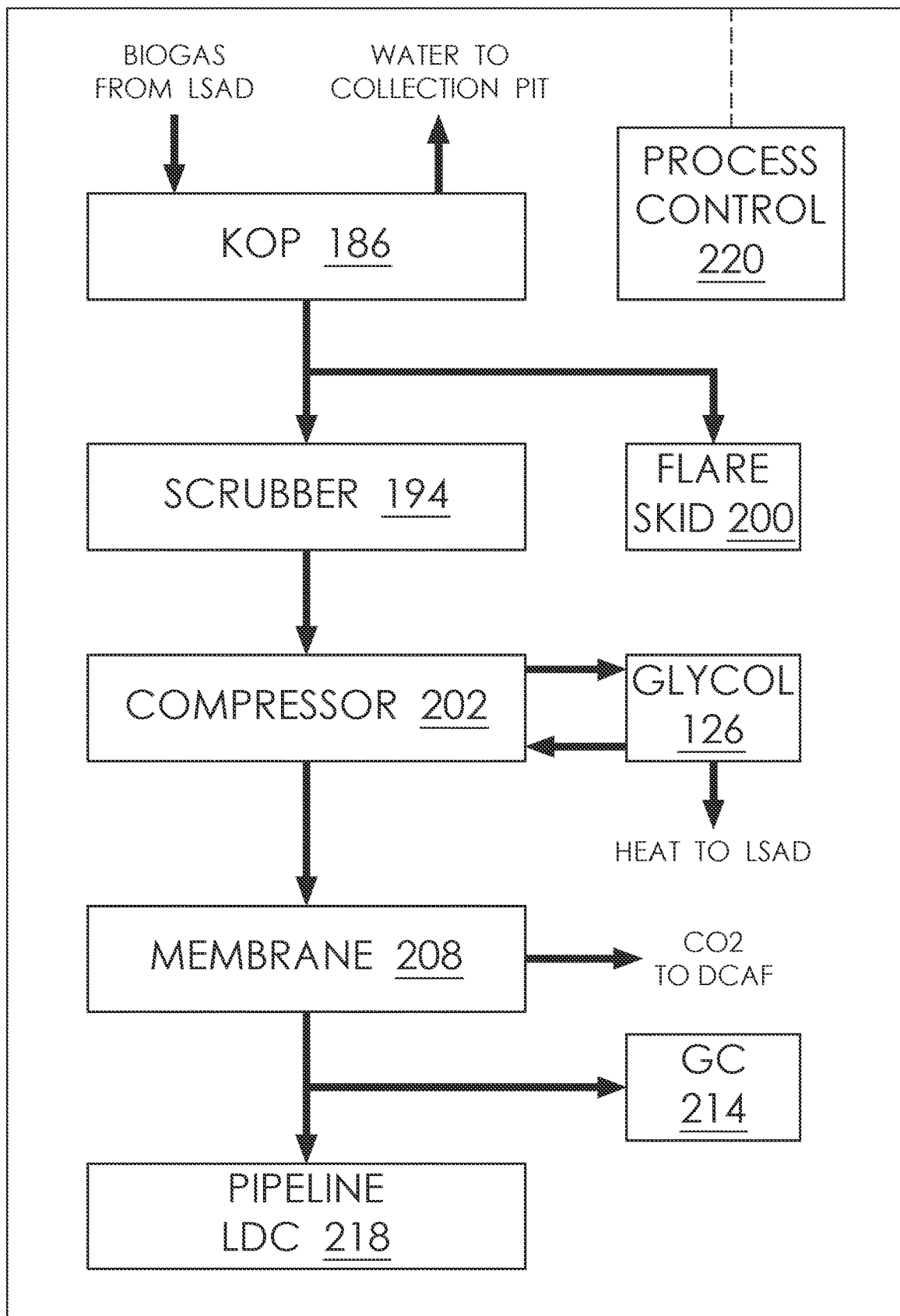
FIG. 23 is a block diagram of the anaerobic waste digestion system of FIG. 1, continued from FIG. 22.

Referring now to FIG. 20, as well as FIG. 1, the sixth phase 218 of the Anaerobic Waste Digestion System 20 is Pipeline Injection 218. The present disclosure utilizes injection into a Local Distribution Company, or LDC pipeline 218. The product gas is 95%-98.5% pure methane, pipeline quality renewable natural gas.

Aspects

It is noted that any of aspects 1-63 may be combined with each other in any suitable combination.

Aspect 1. An anaerobic waste digestion system for use in connection with a source of agricultural animal waste, for generating methane from the animal waste by anaerobic digestion using bacteria, the waste being a water-based slurry having solid particles larger than a predetermined size unsuitable for digestion, the slurry having solid particles smaller than the predetermined size suitable for digestion, the anaerobic waste digestion system comprising a first phase particle separator, including a screen separator adapted for receiving the slurry, the screen separator being adapted for removing suspended solids greater in size than the predetermined size, the first phase particle separator being adapted for allowing passage therethrough of the slurry; a second phase particle separator including an electrocoagulation unit connected in fluid communication with the screen separator for electrochemically inducing hydrolysis of the slurry, so as to cause particles to settle out of the slurry, the electrocoagulation unit being adapted for allowing passage therethrough of the slurry; a third phase particle separator including a dissolved carbon air flotation separator connected in fluid communication with the electrocoagulation unit, the dissolved carbon air flotation separator having a $CO_2$ bubbler for separating by flotation the particles larger than the predetermined size from the particles smaller than the predetermined size, the dissolved carbon air flotation separator being adapted for allowing passage therethrough of the particles smaller than the predetermined size as feedstock; a fourth phase gas producer including at least one low solids anaerobic digester connected in fluid communication with the dissolved carbon air flotation separator, wherein influent enters the anaerobic digester as feedstock, biogas exits as a product, effluent exits as wastewater, and slurry exits as settled solids, the digester having a heat exchanger for heating the bacteria, the digester having at least one biocurtain adjacent the heat exchanger for growing the bacteria, the anaerobic digester being adapted for allowing passage therethrough of the biogas; a fifth phase gas refiner including a membrane module connected in fluid communication with the anaerobic digester for removing heavy hydrocarbons, $CO_2$, and contaminant liquids, the fifth phase gas refiner being adapted for allowing passage therethrough of the biogas; and a process control operatively connected to the anaerobic waste digestion system for controlling the anaerobic waste digestion system; wherein the predetermined particle size ranges from about 50µ to about 200µ.

Aspect 2. The anaerobic waste digestion system in accordance with aspect 1, wherein the first phase particle separator further comprises at least one equalization tank adapted for attachment to the animal waste source for receiving the slurry; at least one slurry pump connected in fluid communication with the equalization tank, for reducing particle size by hydraulic shear; the screen separator being connected in fluid communication with the equalization tank and the slurry pump; and a solids tank connected in communication with the screen separator, for receiving the suspended solids greater in size than the predetermined size.

Aspect 3. The anaerobic waste digestion system in accordance with aspect 1 or 2, wherein the first phase particle separator further comprises a sand lane adapted for attachment to the animal waste source for receiving the animal waste and bedding sand and water, wherein the bedding sand is separated from the animal waste to form the slurry; an equalization pit connected in fluid communication with the sand lane for receiving the slurry, the equalization pit being adapted for allowing passage therethrough of the slurry to the equalization tank; and a lagoon connected in fluid communication with the sand lane for supplying the water to the sand lane.

Aspect 4. The anaerobic waste digestion system in accordance with any of aspects 1-3, wherein the at least one equalization tank and the at least one slurry pump further comprises a first equalization tank; a first slurry pump adapted for receiving slurry from the first equalization tank and returning the slurry to the first equalization tank, so as to reduce particle size by hydraulic shear, the first slurry pump being adapted for discharging the slurry to the screen separator; a second equalization tank; and a second slurry pump adapted for receiving slurry from the second equalization tank and returning the slurry to the second equalization tank, so as to reduce particle size by hydraulic shear, the second slurry pump being adapted for discharging the slurry to the screen separator; wherein one of the first and second equalization tank is adapted for receiving slurry while the other equalization tank is discharging.

Aspect 5. The anaerobic waste digestion system in accordance with any of aspects 1-4, wherein the first phase particle separator further comprises a high phosphorus solids tank for receiving high phosphorus solids removed by the screen separator.

Aspect 6. The anaerobic waste digestion system in accordance with any of aspects 1-5, wherein the electrocoagulation unit further comprises a collection basin including an outlet wall extending between an upper edge and a lower edge; an internal baffle adjacent the outlet wall; a sloping floor; a first outlet disposed adjacent the outlet wall upper edge adapted for discharging slurry particles smaller than the predetermined size; a second outlet disposed below the first outlet and adjacent the internal baffle adapted for discharging slurry particles larger than the particles discharged by the first outlet; and a third outlet disposed below the second outlet and adjacent the sloping floor for discharging slurry particles smaller than the predetermined size and larger than the predetermined size.

Aspect 7. The anaerobic waste digestion system in accordance with any of aspects 1-6, wherein influent entering the dissolved carbon air flotation separator comprises influent slurry, effluent exiting the dissolved carbon air flotation separator comprises feedstock, and slurry exiting the dissolved carbon air flotation separator comprises particles larger than the predetermined size, wherein the dissolved carbon air flotation separator further comprises at least one adjusting baffle disposed so as to cause the influent slurry to flow through the adjusting baffle, and adapted for adjusting cross-sectional flow area, so as to regulate a flow rate of the influent slurry; a separation zone disposed downstream of the adjusting baffle, wherein the slurry particles larger than the predetermined size are separated from the wastewater feedstock particles generally smaller than the predetermined size; at least one sludge hopper for removing the slurry particles larger than the predetermined size, which are sinking; and a conveyor with at least one blade for removing the slurry particles larger than the predetermined size, which are floating, wherein the slurry particles larger than the predetermined size are returned to the first phase particle separator.

Aspect 8. The anaerobic waste digestion system in accordance with any of aspects 1-7, wherein the dissolved carbon air flotation separator further comprises a clear well for receiving feedstock particles generally smaller than the predetermined size; a plurality of adjusting baffles and separation zones, the adjusting baffles being adapted to cause a residence time and a hydrodynamic trajectory of the influent slurry particles in the separation zones to vary with the flow rate of the influent slurry so as to cause particles larger than the predetermined size to separate from the influent flow and move downward, and to allow particles smaller than the predetermined size to move laterally into the clear well; a sludge manifold disposed below the separation zones for receiving particles larger than the predetermined size, the sludge manifold being adapted to convey the slurry particles larger than the predetermined size to the screen separator; a plurality of sludge hoppers disposed below the separation zones for directing downward moving particles into the sludge manifold; a $CO_2$ manifold connected in fluid communication with the separation zones for admitting $CO_2$ bubbles into the separation zones, so as to cause slurry particles larger than the predetermined size to float upward, the $CO_2$ manifold being in fluid communication with the membrane module, so as to receive $CO_2$ from the membrane module; a scum hopper adapted to receive floating slurry particles from the conveyor and convey the particles to the sludge manifold; the conveyor includes a plurality of blades to move floating slurry particles into the scum hopper; and a seeding line connected in fluid communication between the screen separator and the anaerobic digester to convey effluent to the anaerobic digester, so as to maintain an active bacteria culture for digestion.

Aspect 9. The anaerobic waste digestion system in accordance with any of aspects 1-8, wherein the anaerobic digester further comprises a digester tank with first and second opposed sidewalls extending between an inlet endwall and an outlet endwall, the digester tank inlet endwall having an influent inlet in fluid communication with the dissolved carbon air flotation separator, the digester tank outlet endwall having an effluent outlet; a sweep jet inlet manifold in fluid communication with the influent inlet for moving settled solids particles across the digester tank; and a settled solids outlet manifold for removing settled solids from the digester tank, the settled solids outlet manifold being connected in fluid communication with the sweep jet inlet manifold.

Aspect 10. The anaerobic waste digestion system in accordance with any of aspects 1-9, wherein the at least one biocurtain further comprises a float pipe, which floats upon a surface of the wastewater, so as to support the biocurtain; two sheets of polymeric material spaced apart, each sheet having alternating ridges and furrows, so as to increase the surface area for bacterial growth, the sheets extending from the float pipe downward to a tank bottom; and the heat exchanger includes a tubing heat exchanger disposed between the two sheets, the heat exchanger being adapted to receive heat from an external heat source and release heat to the two sheets, so as to promote bacterial growth.

Aspect 11. The anaerobic waste digestion system in accordance with any of aspects 1-10, wherein the external heat source is a compressor; and the tubing heat exchanger further comprises a heat exchange fluid for absorbing waste heat from the compressor and releasing the heat to the biocurtain sheets, so as to maintain the bacteria at an optimum temperature.

Aspect 12. The anaerobic waste digestion system in accordance with any of aspects 1-11, wherein the anaerobic digester further comprises a plurality of biocurtains spaced apart from the inlet endwall to the outlet endwall, every other biocurtain extending from a proximal end adjacent the first sidewall to a distal end adjacent the second sidewall and spaced apart from the second sidewall by a predetermined flow space, each remaining biocurtain extending from a proximal end adjacent the second sidewall to a distal end adjacent the first sidewall and spaced apart from the first sidewall by the flow space, each flow space extending from the tank bottom to the wastewater surface, the biocurtains and spaces alternating so as to provide a flow of feedstock around each of the plurality of biocurtains and through the digester; a heat exchange fluid for absorbing heat from the heat source; a heat supply fluid manifold in fluid communication with each tubing heat exchanger and the heat source, for conveying the heat exchange fluid to each tubing heat exchanger; and a heat return fluid manifold in fluid communication with each tubing heat exchanger and the heat source, for returning the heat exchange fluid to the heat source.

Aspect 13. The anaerobic waste digestion system in accordance with any of aspects 1-12, wherein the anaerobic digester further comprises a plurality of sweep jet nozzles spaced apart along the sweep jet inlet manifold, the nozzles being adapted for directing influent across the tank bottom, so as to cause settled solids to flow across the tank bottom to the settled solids outlet manifold; and a plurality of settled solids nozzles spaced apart along the settled solids outlet manifold for receiving settled solids flowing across the tank bottom.

Aspect 14. The anaerobic waste digestion system in accordance with any of aspects 1-13, wherein the fifth phase gas refiner further comprises a knock out pot connected in fluid communication with the anaerobic digester, the knock out pot being adapted for removing entrained droplets of water from the biogas; a scrubber connected in fluid communication with the knock out pot for removing water vapor, particulates, and contaminant gas from the biogas; and a compressor connected in fluid communication with the scrubber and the membrane module.

Aspect 15. The anaerobic waste digestion system in accordance with any of aspects 1-14, wherein the fifth phase gas refiner further comprises a flare skid connected in fluid communication with the scrubber; and a gas chromatograph connected in fluid communication with the membrane module for monitoring the biogas composition.

Aspect 16. The anaerobic waste digestion system in accordance with any of aspects 1-15, further comprising a collection pit connected in fluid communication with the anaerobic digester effluent outlet and the knock out pot for receiving the effluent from the anaerobic digester and the water from the knock out pot; and at least one lagoon connected in fluid communication with the collection pit for receiving the effluent and water therefrom, the lagoon being connected in fluid communication with the first phase particle separator for conveying the water thereto.

Aspect 17. The anaerobic waste digestion system in accordance with any of aspects 1-16, wherein the anaerobic digester further comprises a digester first cell having a first cell inlet and a first cell outlet, the first cell being adapted for selective connections upstream and downstream; a digester second cell having a second cell inlet and a second cell outlet, the second cell being adapted for selective connections upstream and downstream; a first cell bypass adapted for selectively connecting the second cell outlet to the first cell inlet; and a second cell bypass adapted for selectively connecting the first cell outlet to the second cell inlet, wherein the first cell and the second cell are selectively connected in fluid communication with the dissolved carbon air flotation separator and the collection pit in a manner selected from the group consisting of: the first cell inlet and the second cell inlet are connected to the dissolved carbon air flotation separator, the first cell outlet and the second cell outlet are connected to the collection pit, the first cell bypass and the second cell bypass are closed; the first cell inlet is connected to the dissolved carbon air flotation separator, and the first cell outlet is connected to the collection pit, the second cell inlet and the second cell outlet are closed, the first cell bypass and the second cell bypass are closed; the second cell inlet is connected to the dissolved carbon air flotation separator, and the second cell outlet is connected to the collection pit, the first cell inlet and the first cell outlet are closed, the first cell bypass and the second cell bypass are closed; the first cell inlet is connected to the dissolved carbon air flotation separator, and the first cell outlet is closed downstream, the second cell inlet is closed upstream and the second cell outlet is connected to the collection pit, the second cell bypass is connected between the first cell outlet and the second cell inlet, and the first cell bypass is closed; and the second cell inlet is connected to the dissolved carbon air flotation separator, and the second cell outlet is closed downstream, the first cell inlet is closed upstream and the first cell outlet is connected to the collection pit, the first cell bypass is connected between the second cell outlet and the first cell inlet, and the second cell bypass is closed.

Aspect 18. The anaerobic waste digestion system in accordance with any of aspects 1-17, further comprising a sixth phase pipeline injector for injecting biogas into a local pipeline system, the sixth phase pipeline injector being connected in fluid communication with the membrane module.

Aspect 19. An anaerobic waste digestion system for use in connection with a source of agricultural animal waste, for generating methane from the animal waste by anaerobic digestion using bacteria, the waste being a water-based slurry having solid particles larger than a predetermined size unsuitable for digestion, the slurry having solid particles smaller than the predetermined size suitable for digestion, the anaerobic waste digestion system comprising a first phase particle separator, including at least one equalization tank adapted for receiving the slurry, the first phase particle separator having at least one slurry pump connected in fluid communication with the equalization tank, for reducing particle size by hydraulic shear, the first phase particle separator having a screen separator connected in fluid communication with the equalization tank and the slurry pump, for removing suspended solids greater in size than the predetermined size, and the first phase particle separator having a solids tank connected in fluid communication with the screen separator, for receiving the suspended solids greater in size than the predetermined size, the first phase particle separator being adapted for allowing passage therethrough of the slurry; a second phase particle separator including an electrocoagulation unit connected in fluid communication with the screen separator for electrochemically inducing hydrolysis of the slurry, so as to cause particles to settle out of the slurry, the electrocoagulation unit being adapted for allowing passage therethrough of the slurry; a third phase particle separator including a dissolved carbon air flotation separator connected in fluid communication with the electrocoagulation unit, the dissolved carbon air flotation separator having a $CO_2$ bubbler for separating by flotation the particles larger than the predetermined size from the particles smaller than the predetermined size, the dissolved carbon air flotation separator being adapted for allowing passage therethrough of the particles smaller than the predetermined size as feedstock; a fourth phase gas producer including at least one low solids anaerobic digester connected in fluid communication with the dissolved carbon air flotation separator, wherein influent enters the anaerobic digester as feedstock, biogas exits as a product, effluent exits as wastewater, and slurry exits as settled solids, the digester having a digester tank with first and second opposed sidewalls extending between an inlet endwall and an outlet endwall, the digester tank inlet endwall having an influent inlet in fluid communication with the dissolved carbon air flotation separator, the digester tank outlet endwall having an effluent outlet, the digester having a heat exchanger for heating the bacteria, the digester having at least one biocurtain adjacent the heat exchanger for growing the bacteria, the biocurtain having alternating ridges and furrows on at least one surface so as to retain the bacteria, the digester having a sweep jet inlet manifold in fluid communication with the influent inlet for moving settled solids particles across the digester tank, the digester having a settled solids outlet manifold for removing settled solids from the digester tank, the settled solids outlet manifold being connected in fluid communication with the sweep jet inlet manifold, the anaerobic digester being adapted for allowing passage therethrough of the biogas; a fifth phase gas refiner including a knock out pot connected in fluid communication with the anaerobic digester, the knock out pot being adapted for removing droplets of water, the fifth phase gas refiner having a scrubber connected in fluid communication with the knock out pot for removing water vapor, particulates, and contaminant gas, the fifth phase gas refiner having a compressor connected in fluid communication with the scrubber, the fifth phase gas refiner having a membrane module connected in fluid communication with the compressor for removing heavy hydrocarbons, $CO_2$, and contaminant liquids, the fifth phase gas refiner having a gas chromatograph for monitoring the biogas composition, the fifth phase gas refiner being adapted for allowing passage therethrough of the biogas; a sixth phase pipeline injector for injecting biogas into a local pipeline system, the sixth phase pipeline injector being connected in fluid communication with the membrane module; and a process control operatively connected to the anaerobic waste digestion system for controlling the anaerobic waste digestion system; wherein the predetermined particle size ranges from about 50μ to about 200μ.

Aspect 20. The anaerobic waste digestion system in accordance with aspect 19, wherein the first phase particle separator further comprises a sand lane adapted for attachment to the animal waste source for receiving the animal waste and bedding sand and water, wherein the bedding sand is separated from the animal waste to form the slurry an equalization pit connected in fluid communication with the sand lane for receiving the slurry, the equalization pit being adapted for allowing passage therethrough of the slurry to the equalization tank; and a lagoon connected in fluid communication with the sand lane for supplying the water to the sand lane.

Aspect 21. The anaerobic waste digestion system in accordance with aspect 19 or 20, wherein the at least one equalization tank and the at least one slurry pump further comprises a first equalization tank; a first slurry pump adapted for receiving slurry from the first equalization tank and returning the slurry to the first equalization tank, so as to reduce particle size by hydraulic shear, the first slurry pump being adapted for discharging the slurry to the screen separator; a second equalization tank; and a second slurry pump adapted for receiving slurry from the second equalization tank and returning the slurry to the second equalization tank, so as to reduce particle size by hydraulic shear, the second slurry pump being adapted for discharging the slurry to the screen separator, wherein one of the first and second equalization tank is adapted for receiving slurry while the other equalization tank is discharging.

Aspect 22. The anaerobic waste digestion system in accordance with any of aspects 19-21, wherein the first phase particle separator further comprises a high phosphorus solids tank for receiving high phosphorus solids removed by the screen separator.

Aspect 23. The anaerobic waste digestion system in accordance with any of aspects 19-22, wherein the electrocoagulation unit further comprises a collection basin, including an outlet wall extending between an upper edge and a lower edge; an internal baffle adjacent the outlet wall; a sloping floor; a first outlet disposed adjacent the outlet wall upper edge adapted for discharging slurry particles smaller than the predetermined size; a second outlet disposed below the first outlet and adjacent the internal baffle adapted for discharging slurry particles larger than the particles discharged by the first outlet; and a third outlet disposed below the second outlet and adjacent the sloping floor for discharging slurry particles smaller than the predetermined size and larger than the predetermined size.

Aspect 24. The anaerobic waste digestion system in accordance with any of aspects 19-23, wherein influent entering the dissolved carbon air flotation separator comprises influent slurry, effluent exiting the dissolved carbon air flotation separator comprises feedstock, and slurry exiting the dissolved carbon air flotation separator comprises particles larger than the predetermined size, wherein the dissolved carbon air flotation separator further comprises at least one adjusting baffle disposed so as to cause the influent slurry to flow through the adjusting baffle, and adapted for adjusting cross-sectional flow area, so as to regulate a flow rate of the influent slurry a separation zone disposed downstream of the adjusting baffle, wherein the slurry particles larger than the predetermined size are separated from the wastewater feedstock particles generally smaller than the predetermined size; at least one sludge hopper for removing the slurry particles larger than the predetermined size, which are sinking; and a conveyor with at least one blade for removing the slurry particles larger than the predetermined size, which are floating, wherein the slurry particles larger than the predetermined size are returned to the first phase particle separator.

Aspect 25. The anaerobic waste digestion system in accordance with any of aspects 19-24, wherein the dissolved carbon air flotation separator further comprises: a clear well for receiving feedstock particles generally smaller than the predetermined size; a plurality of adjusting baffles and separation zones, the adjusting baffles being adapted to cause a residence time and a hydrodynamic trajectory of the influent slurry particles in the separation zones to vary with the flow rate of the influent slurry so as to cause particles larger than the predetermined size to separate from the influent flow and move downward, and to allow particles smaller than the predetermined size to move laterally into the clear well; a sludge manifold disposed below the separation zones for receiving particles larger than the predetermined size, the sludge manifold being adapted to convey the slurry particles larger than the predetermined size to the screen separator; a plurality of sludge hoppers disposed below the separation zones for directing downward moving particles into the sludge manifold; a $CO_2$ manifold connected in fluid communication with the separation zones for admitting $CO_2$ bubbles into the separation zones, so as to cause slurry particles larger than the predetermined size to float upward, the $CO_2$ manifold being in fluid communication with the membrane module, so as to receive $CO_2$ from the membrane module; a scum hopper adapted to receive floating slurry particles from the conveyor and convey the particles to the sludge manifold; the conveyor includes a plurality of blades to move floating slurry particles into the scum hopper; and a seeding line connected in fluid communication between the screen separator and the anaerobic digester to convey effluent to the anaerobic digester, so as to maintain an active bacteria culture for digestion.

Aspect 26. The anaerobic waste digestion system in accordance with any of aspects 19-25, wherein the at least one biocurtain further comprises a float pipe, which floats upon a surface of the wastewater, so as to support the biocurtain; two sheets of polymeric material spaced apart, each sheet having alternating ridges and furrows, so as to increase the surface area for bacterial growth, the sheets extending from the float pipe downward to a tank bottom; and the heat exchanger includes a tubing heat exchanger disposed between the two sheets, the heat exchanger being adapted to receive heat from an external heat source and release heat to the two sheets, so as to promote bacterial growth.

Aspect 27. The anaerobic waste digestion system in accordance with any of aspects 19-26, wherein the external heat source is the compressor; and the tubing heat exchanger further comprises a heat exchange fluid for absorbing waste heat from the compressor and releasing the heat to the biocurtain sheets, so as to maintain the bacteria at an optimum temperature.

Aspect 28. The anaerobic waste digestion system in accordance with any of aspects 19-27, wherein the anaerobic digester further comprises a plurality of biocurtains spaced apart from the inlet endwall to the outlet endwall, every other biocurtain extending from a proximal end adjacent the first sidewall to a distal end adjacent the second sidewall and spaced apart from the second sidewall by a predetermined flow space, each remaining biocurtain extending from a proximal end adjacent the second sidewall to a distal end adjacent the first sidewall and spaced apart from the first sidewall by the flow space, each flow space extending from the tank bottom to the wastewater surface, the biocurtains and spaces alternating so as to provide a flow of feedstock around each of the plurality of biocurtains and through the digester; a heat exchange fluid for absorbing heat from the heat source; a heat supply fluid manifold in fluid communication with each tubing heat exchanger and the heat source, for conveying the heat exchange fluid to each tubing heat exchanger; and a heat return fluid manifold in fluid communication with each tubing heat exchanger and the heat source, for returning the heat exchange fluid to the heat source.

Aspect 29. The anaerobic waste digestion system in accordance with any of aspects 19-28, wherein the anaerobic digester further comprises a plurality of sweep jet nozzles spaced apart along the sweep jet inlet manifold, the nozzles being adapted for directing influent across the tank bottom, so as to cause settled solids to flow across the tank bottom to the settled solids outlet manifold; and a plurality of settled solids nozzles spaced apart along the settled solids outlet manifold for receiving settled solids flowing across the tank bottom.

Aspect 30. The anaerobic waste digestion system in accordance with any of aspects 19-29, wherein the anaerobic digester further comprises a digester first cell having a first cell inlet and a first cell outlet, the first cell being adapted for selective connections upstream and downstream; a digester second cell having a second cell inlet and a second cell outlet, the second cell being adapted for selective connections upstream and downstream; a first cell bypass adapted for selectively connecting the second cell outlet to the first cell inlet; and a second cell bypass adapted for selectively connecting the first cell outlet to the second cell inlet, wherein the first cell and the second cell are selectively connected in fluid communication with the dissolved carbon air flotation separator and the collection pit in a manner selected from the group consisting of the first cell inlet and the second cell inlet are connected to the dissolved carbon air flotation separator, the first cell outlet and the second cell outlet are connected to the collection pit, the first cell bypass and the second cell bypass are closed; the first cell inlet is connected to the dissolved carbon air flotation separator, and the first cell outlet is connected to the collection pit, the second cell inlet and the second cell outlet are closed, the first cell bypass and the second cell bypass are closed; the second cell inlet is connected to the dissolved carbon air flotation separator, and the second cell outlet is connected to the collection pit, the first cell inlet and the first cell outlet are closed, the first cell bypass and the second cell bypass are closed; the first cell inlet is connected to the dissolved carbon air flotation separator, and the first cell outlet is closed downstream, the second cell inlet is closed upstream and the second cell outlet is connected to the collection pit, the second cell bypass is connected between the first cell outlet and the second cell inlet, and the first cell bypass is closed; and the second cell inlet is connected to the dissolved carbon air flotation separator, and the second cell outlet is closed downstream, the first cell inlet is closed upstream and the first cell outlet is connected to the collection pit, the first cell bypass is connected between the second cell outlet and the first cell inlet, and the second cell bypass is closed.

Aspect 31. The anaerobic waste digestion system of in accordance with any of aspects 19-30, further comprising a collection pit connected in fluid communication with the anaerobic digester effluent outlet and the knock out pot for receiving the wastewater therefrom; and at least one lagoon connected in fluid communication with the collection pit for receiving the wastewater therefrom, the lagoon being connected in fluid communication with the first phase particle separator for conveying the wastewater thereto.

Aspect 32. The anaerobic waste digestion system in accordance with any of aspects 19-31, wherein the fifth phase gas refiner further comprises a flare skid connected in fluid communication with the scrubber; and the gas chromatograph being connected in fluid communication with the membrane module.

Aspect 33. A method for generating methane from animal waste by anaerobic digestion, for use in connection with a source of agricultural animal waste, the waste being a water-based slurry having solid particles larger than a predetermined size unsuitable for digestion, the slurry having solid particles smaller than the predetermined size suitable for digestion, the method comprising providing a first phase particle separator downstream of the source of agricultural animal waste; juxtaposing a screen separator with the first phase particle separator; receiving the slurry into the screen separator, and removing suspended solids greater in size than the solid particles predetermined size with the screen separator; allowing passage of the slurry through first phase particle separator; providing a second phase particle separator downstream of the first phase particle separator; juxtaposing an electrocoagulation unit with the second phase particle separator, and connecting the electrocoagulation unit in fluid communication with the screen separator; receiving the slurry into the electrocoagulation unit, and electrochemically hydrolyzing and destabilizing the slurry with the electrocoagulation unit, thereby causing the solid particles to stratify and settle out of the slurry; allowing passage of the slurry through the electrocoagulation unit; providing a third phase particle separator downstream of the second phase particle separator; juxtaposing a dissolved carbon air flotation separator with the third phase particle separator and connecting the dissolved carbon air flotation separator in fluid communication with the electrocoagulation unit; receiving the slurry into the dissolved carbon air flotation separator; introducing $CO_2$ bubbles into the dissolved carbon air flotation separator, and dissolving the $CO_2$ into the effluent, thereby increasing methane production; separating by flotation the solid particles larger than the predetermined size from the solid particles smaller than the predetermined size with the $CO_2$ bubbles; allowing passage through the dissolved carbon air flotation separator of the solid particles smaller than the solid particles predetermined size as feedstock; providing a fourth phase gas producer downstream of the third phase particle separator; juxtaposing at least one low solids anaerobic digester with the fourth phase gas producer and connecting the anaerobic digester in fluid communication with the dissolved carbon air flotation separator; receiving influent into the anaerobic digester as feedstock; producing methane biogas by anaerobically digesting the feedstock with bacteria; disposing at least one biocurtain within the digester and growing the bacteria on at least one surface of the biocurtain; juxtaposing a heat exchanger with the biocurtain, and heating the bacteria with the heat exchanger; allowing passage through the anaerobic digester of the biogas as a product; allowing passage through the anaerobic digester of effluent as wastewater; providing a fifth phase gas refiner downstream of the fourth phase gas producer; juxtaposing a membrane module with the fifth phase gas refiner, connecting the membrane module in fluid communication with the anaerobic digester, and removing heavy hydrocarbons, $CO_2$, and contaminant liquids with the membrane module; conveying $CO_2$ from the membrane module to the dissolved carbon air flotation separator; allowing passage through the fifth phase gas refiner of the biogas; providing a process control, operatively connecting the process control to the anaerobic waste digestion system, and controlling the anaerobic waste digestion system with the process control; and processing the slurry having the predetermined solid particle size ranging from about 50μ to about 200μ.

Aspect 34. The method in accordance with aspect 33, further comprising juxtaposing at least one equalization tank with the first phase particle separator, and connecting the equalization tank in fluid communication with the animal waste source; receiving the slurry into the equalization tank; juxtaposing at least one slurry pump with the first phase particle separator, and connecting the slurry pump in fluid communication with the equalization tank; circulating the slurry in the equalization tank, and reducing the solid particles size by hydraulic shear with the slurry pump; connecting the screen separator in fluid communication with the equalization tank and the slurry pump; juxtaposing a solids tank with the first phase particle separator, and connecting the solids tank in fluid communication with the screen separator; and receiving the solid particles greater in size than the solid particles predetermined size into the solids tank.

Aspect 35. The method in accordance with aspect 33 or 34, further comprising providing a sand lane downstream of the animal waste source, and connecting the sand lane to the animal waste source; receiving the animal waste and bedding sand and water in the sand lane, and separating the bedding sand from the animal waste to form the slurry; providing an equalization pit, connecting the equalization pit in fluid communication with the sand lane, and receiving the slurry in the equalization pit; receiving the animal waste and water in the equalization pit to form the slurry; and allowing passage of the slurry through the sand lane and through the equalization pit to the equalization tank.

Aspect 36. The method in accordance with any of aspects 33-35, wherein the at least one equalization tank further comprises a first equalization tank and a second equalization tank; the at least one slurry pump further comprises a first slurry pump and a second slurry pump; and the method further comprises receiving the slurry into the first equalization tank; connecting the first slurry pump in fluid communication with the first equalization tank; pumping the slurry from the first equalization tank through the first slurry pump and returning the slurry to the first equalization tank, thereby reducing the solid particle size by hydraulic shear; discharging the slurry to the screen separator with the first slurry pump; receiving the slurry into the second equalization tank; connecting the second slurry pump in fluid communication with the second equalization tank; pumping the slurry from the second equalization tank through the second slurry pump and returning the slurry to the second equalization tank, thereby reducing the solid particle size by hydraulic shear; discharging the slurry to the screen separator with the second slurry pump; and receiving the slurry into one of the first and second equalization tank while discharging the slurry from the other equalization tank.

Aspect 37. The method in accordance with any of aspects 33-36, further comprising juxtaposing a high phosphorus solids tank with the first phase particle separator, and connecting the high phosphorus solids tank in fluid communication with the screen separator and the dissolved carbon air flotation separator; and receiving high phosphorus solid particles greater in size than the predetermined solid particle size into the high phosphorus solids tank.

Aspect 38. The method in accordance with any of aspects 33-37, wherein the electrocoagulation unit further comprises a collection basin having an outlet wall extending between an upper edge and a lower edge, the collection basin having an internal baffle adjacent the outlet wall, the collection basin having a sloping floor; and the method further comprises disposing a first outlet adjacent the outlet wall upper edge and adapting the first outlet for discharging slurry particles smaller than the predetermined solid particle size; disposing a second outlet below the first outlet and adjacent the internal baffle and adapting the second outlet for discharging slurry particles larger than the particles discharged by the first outlet; and disposing a third outlet below the second outlet and adjacent the sloping floor and allowing passage through the third outlet of slurry particles smaller than the predetermined solid particle size and larger than the predetermined solid particle size.

Aspect 39. The method in accordance with any of aspects 33-38, wherein influent entering the dissolved carbon air flotation separator comprises influent slurry, effluent exiting the dissolved carbon air flotation separator comprises feedstock, and slurry exiting the dissolved carbon air flotation separator comprises particles larger than the predetermined solid particle size; and the method further comprises disposing at least one adjusting baffle within the dissolved carbon air flotation separator, and directing the influent slurry to flow through the adjusting baffle; adjusting a cross-sectional flow area of the at least one adjusting baffle, thereby regulating a flow rate of the influent slurry; disposing a separation zone downstream of the adjusting baffle; separating the slurry particles larger than the predetermined solid particle size from the wastewater and feedstock particles generally smaller than the predetermined solid particle size within the separation zone; providing at least one sludge hopper downstream of the separation zone, and receiving the slurry particles larger than the predetermined solid particle size, which are sinking, into the sludge hopper; disposing a conveyor with at least one blade above the separation zone, and moving the slurry particles larger than the predetermined solid particle size, which are floating, into the sludge hopper; and conveying the slurry particles larger than the predetermined solid particle size to the first phase particle separator.

Aspect 40. The method in accordance with any of aspects 33-39, wherein the dissolved carbon air flotation separator further comprises a plurality of adjusting baffles and separation zones, the conveyor includes a plurality of blades; and the method further comprises disposing a clear well downstream of the separation zones and receiving feedstock particles generally smaller than the predetermined solid particle size into the clear well; adjusting a cross-sectional flow area of the plurality of adjusting baffles, thereby regulating a flow rate of the influent slurry; causing a residence time and a hydrodynamic trajectory of the influent slurry particles in the separation zones to vary with the flow rate of the influent slurry, thereby causing particles larger than the predetermined solid particle size to separate from the influent flow and move downward, and allowing particles smaller than the predetermined solid particle size to move laterally into the clear well; disposing a plurality of sludge hoppers below the separation zones and receiving downward moving particles into the sludge hoppers; disposing a sludge manifold below the separation zones, connecting the sludge manifold in fluid communication with the sludge hoppers, and receiving particles larger than the predetermined solid particle size into the sludge manifold; disposing a $CO_2$ manifold adjacent the separation zones, connecting the $CO_2$ manifold in fluid communication with the separation zones, and admitting $CO_2$ bubbles into the separation zones; connecting the $CO_2$ manifold in fluid communication with the membrane module, and receiving $CO_2$ into the $CO_2$ manifold from the membrane module; causing slurry particles larger than the predetermined solid particle size to float upward with the $CO_2$ bubbles; disposing a scum hopper adjacent the separation zones, and connecting the scum hopper in fluid communication with the sludge manifold; moving the floating slurry particles larger than the predetermined solid particle size into the scum hopper with the conveyor blades, and conveying the particles to the sludge manifold; connecting the sludge manifold in fluid communication with the screen separator, and conveying the slurry to the screen separator; conveying effluent with a seeding line from the screen separator to the anaerobic digester; and maintaining an active bacteria culture for digestion by conveying effluent to the anaerobic digester.

Aspect 41. The method in accordance with any of aspects 33-40, further comprising moving settled solids particles across the anaerobic digester with a sweep jet; removing the settled solids from the anaerobic digester, and conveying the settled solids back to the sweep jet; and conveying a portion of the settled solids to the first phase particle separator, thereby controlling the solids residence time.

Aspect 42. The method in accordance with any of aspects 33-41, wherein the at least one biocurtain further comprises a float pipe, and two sheets of polymeric material spaced apart; the heat exchanger further comprises a tubing heat exchanger disposed between the two sheets; and the method further comprises receiving heat into the heat exchanger from an external heat source, and releasing the heat to the two sheets, thereby promoting growth of the bacteria; forming alternating ridges and furrows on each of the two sheets, thereby increasing the surface area for growth of the bacteria; floating the float pipe upon a surface of the wastewater, and supporting the biocurtain with the float pipe; and extending the sheets downward from the float pipe, and anchoring the sheets to a tank bottom.

Aspect 43. The method in accordance with any of aspects 33-42, wherein the external heat source further comprises the compressor; the tubing heat exchanger further comprises a heat exchange fluid; and the method further comprises absorbing waste heat from the compressor with the heat exchange fluid and releasing the heat to the biocurtain sheets, thereby maintaining the bacteria at an optimum temperature.

Aspect 44. The method in accordance with any of aspects 33-43, wherein the anaerobic digester further comprises a plurality of biocurtains spaced apart along the anaerobic digester; the tubing heat exchanger further comprises a heat exchange fluid; and the method further comprises flowing the feedstock through the digester and around each of the plurality of biocurtains; absorbing heat from the heat source with the heat exchange fluid and releasing the heat to the biocurtain sheets, thereby maintaining the bacteria at an optimum temperature; and returning the heat exchange fluid to the heat source.

Aspect 45. The method in accordance with any of aspects 33-44, further comprising disposing a plurality of sweep jet nozzles spaced apart along a sweep jet inlet manifold; directing the influent across the tank bottom with the nozzles, thereby causing the settled solids to flow across the tank bottom to a settled solids outlet manifold; and disposing a plurality of settled solids nozzles spaced apart along the settled solids outlet manifold, and receiving the settled solids flowing across the tank bottom into the settled solids outlet manifold.

Aspect 46. The method in accordance with any of aspects 33-45, further comprising juxtaposing a knock out pot with the fifth phase gas refiner, and connecting the knock out pot in fluid communication with the anaerobic digester; receiving the biogas into the knock out pot, and removing entrained droplets of water from the biogas with the knock out pot; providing a collection pit and connecting the collection pit in fluid communication with the anaerobic digester and the knock out pot; receiving the effluent into the collection pit from the anaerobic digester; receiving the water into the collection pit from the knock out pot; providing at least one lagoon and connecting the lagoon in fluid communication with the collection pit and the first phase particle separator; andreceiving the water into the lagoon from the collection pit, and conveying the water from the lagoon to the first phase particle separator.

Aspect 47. The method in accordance with any of aspects 33-46, wherein the anaerobic digester further comprises a digester first cell having a first cell inlet and a first cell outlet, the first cell being adapted for selective connections upstream and downstream; a digester second cell having a second cell inlet and a second cell outlet, the second cell being adapted for selective connections upstream and downstream; a first cell bypass adapted for selectively connecting the second cell outlet to the first cell inlet; and a second cell bypass adapted for selectively connecting the first cell outlet to the second cell inlet; and the method further comprises selectively connecting the first cell and the second cell in fluid communication with the dissolved carbon air flotation separator and the collection pit in a manner selected from the group consisting of connecting the first cell inlet and the second cell inlet to the dissolved carbon air flotation separator, connecting the first cell outlet and the second cell outlet to the collection pit, and closing the first cell bypass and the second cell bypass; connecting the first cell inlet to the dissolved carbon air flotation separator, connecting the first cell outlet to the collection pit, closing the second cell inlet and the second cell outlet, and closing the first cell bypass and the second cell bypass; connecting the second cell inlet to the dissolved carbon air flotation separator, connecting the second cell outlet to the collection pit, closing the first cell inlet and the first cell outlet, and closing the first cell bypass and the second cell bypass; connecting the first cell inlet to the dissolved carbon air flotation separator, closing the first cell outlet downstream, closing the second cell inlet upstream, connecting the second cell outlet to the collection pit, connecting the second cell bypass between the first cell outlet and the second cell inlet, and closing the first cell bypass; and connecting the second cell inlet to the dissolved carbon air flotation separator, closing the second cell outlet downstream, closing the first cell inlet upstream, connecting the first cell outlet to the collection pit, connecting the first cell bypass between the second cell outlet and the first cell inlet, and closing the second cell bypass.

Aspect 48. The method in accordance with any of aspects 33-47, further comprising juxtaposing a scrubber with the fifth phase gas refiner, connecting the scrubber in fluid communication with the knock out pot, and removing water vapor, particulates, and contaminant gas with the scrubber; and juxtaposing a compressor with the fifth phase gas refiner, connecting the compressor in fluid communication with the scrubber, and compressing the biogas with the compressor.

Aspect 49. The method in accordance with any of aspects 33-48, further comprising juxtaposing a flare skid with the fifth phase gas refiner, connecting the flare skid in fluid communication with the knock out pot, and adapting the flare skid for removing biogas; and juxtaposing a gas chromatograph with the fifth phase gas refiner, connecting the gas chromatograph in fluid communication with the membrane module, and monitoring the biogas composition with the gas chromatograph.

Aspect 50. The method in accordance with any of aspects 33-49, further comprising providing a sixth phase pipeline injector, connecting the pipeline injector in fluid communication with the membrane module, and injecting the biogas into a local pipeline system with the pipeline injector.

Aspect 51. A method for generating methane from animal waste by anaerobic digestion, for use in connection with a source of agricultural animal waste, the waste being a water-based slurry having solid particles larger than a predetermined size unsuitable for digestion, the slurry having solid particles smaller than the predetermined size suitable for digestion, the method comprising providing a first phase particle separator downstream of the source of agricultural animal waste; juxtaposing at least one equalization tank with the first phase particle separator, and receiving the slurry into the equalization tank; juxtaposing at least one slurry pump with the first phase particle separator, and connecting the slurry pump in fluid communication with the equalization tank; circulating the slurry in the equalization tank, and reducing the solid particles size by hydraulic shear with the slurry pump; juxtaposing a screen separator with the first phase particle separator, and connecting the screen separator in fluid communication with the equalization tank and the slurry pump; receiving the slurry into the screen separator, and removing suspended solids greater in size than the solid particles predetermined size with the screen separator; juxtaposing a solids tank with the first phase particle separator, and connecting the solids tank in fluid communication with the screen separator; receiving the solid particles greater in size than the solid particles predetermined size into the solids tank; allowing passage of the slurry through first phase particle separator; providing a second phase particle separator downstream of the first phase particle separator; juxtaposing an electrocoagulation unit with the second phase particle separator, and connecting the electrocoagulation unit in fluid communication with the screen separator; receiving the slurry into the electrocoagulation unit, and electrochemically hydrolyzing and destabilizing the slurry with the electrocoagulation unit, thereby causing the solid particles to stratify and settle out of the slurry; allowing passage of the slurry through the electrocoagulation unit; providing a third phase particle separator downstream of the second phase particle separator; juxtaposing a dissolved carbon air flotation separator with the third phase particle separator and connecting the dissolved carbon air flotation separator in fluid communication with the electrocoagulation unit; receiving the slurry into the dissolved carbon air flotation separator; introducing $CO_2$ bubbles into the dissolved carbon air flotation separator, and dissolving the $CO_2$ into the effluent, thereby increasing methane production; separating by flotation the solid particles larger than the predetermined size from the solid particles smaller than the predetermined size with the $CO_2$ bubbles; allowing passage through the dissolved carbon air flotation separator of the solid particles smaller than the solid particles predetermined size as feedstock; providing a fourth phase gas producer downstream of the third phase particle separator; juxtaposing at least one low solids anaerobic digester with the fourth phase gas producer and connecting the anaerobic digester in fluid communication with the dissolved carbon air flotation separator; receiving influent into the anaerobic digester as feedstock; producing methane biogas by anaerobically digesting the feedstock with bacteria; disposing at least one biocurtain within the digester for growing the bacteria, and retaining the bacteria on at least one surface of the biocurtain with alternating ridges and furrows on the at least one surface; juxtaposing a heat exchanger with the biocurtain, and heating the bacteria with the heat exchanger; moving settled solids particles across the anaerobic digester with a sweep jet; removing the settled solids from the anaerobic digester, and conveying the settled solids back to the sweep jet; allowing passage through the anaerobic digester of the biogas as a product; allowing passage through the anaerobic digester of effluent as wastewater; providing a fifth phase gas refiner downstream of the fourth phase gas producer; juxtaposing a knock out pot with the fifth phase gas refiner, and connecting the knock out pot in fluid communication with the anaerobic digester; receiving the biogas into the knock out pot, and removing the entrained droplets of water from the biogas with the knock out pot; juxtaposing a flare skid with the fifth phase gas refiner, connecting the flare skid in fluid communication with the knock out pot, and adapting the flare skid for removing biogas; juxtaposing a scrubber with the fifth phase gas refiner, connecting the scrubber in fluid communication with the knock out pot, and removing the water vapor, particulates, and contaminant gas with the scrubber; juxtaposing a compressor with the fifth phase gas refiner, connecting the compressor in fluid communication with the scrubber, and compressing the biogas with the compressor; juxtaposing a membrane module with the fifth phase gas refiner, connecting the membrane module in fluid communication with the compressor, and removing heavy hydrocarbons, $CO_2$, and contaminant liquids with the membrane module; conveying $CO_2$ from the membrane module to the dissolved carbon air flotation separator; juxtaposing a gas chromatograph with the fifth phase gas refiner, connecting the gas chromatograph in fluid communication with the membrane module, and monitoring the biogas composition with the gas chromatograph; allowing passage through the fifth phase gas refiner of the biogas; providing a sixth phase pipeline injector, connecting the pipeline injector in fluid communication with the membrane module, and injecting the biogas into a local pipeline system with the pipeline injector; providing a process control, operatively connecting the process control to the anaerobic waste digestion system, and controlling the anaerobic waste digestion system with the process control; and processing the slurry having the predetermined solid particle size ranging from about 50μ to about 200μ.

Aspect 52. The method in accordance with aspect 51, further comprising providing a sand lane downstream of the animal waste source, and connecting the sand lane to the animal waste source; receiving the animal waste and bedding sand and water in the sand lane, and separating the bedding sand from the animal waste to form the slurry; providing an equalization pit, connecting the equalization pit in fluid communication with the sand lane, and receiving the slurry in the equalization pit; receiving the animal waste and water in the equalization pit to form the slurry; and allowing passage of the slurry through the sand lane and through the equalization pit to the equalization tank.

Aspect 53. The method in accordance with aspect 51 or 52, wherein the at least one equalization tank further comprises a first equalization tank and a second equalization tank; the at least one slurry pump further comprises a first slurry pump and a second slurry pump; and the method further comprises receiving the slurry into the first equalization tank; connecting the first slurry pump in fluid communication with the first equalization tank; pumping the slurry from the first equalization tank through the first slurry pump and returning the slurry to the first equalization tank, thereby reducing the solid particle size by hydraulic shear; discharging the slurry to the screen separator with the first slurry pump; receiving the slurry into the second equalization tank; connecting the second slurry pump in fluid communication with the second equalization tank; pumping the slurry from the second equalization tank through the second slurry pump and returning the slurry to the second equalization tank, thereby reducing the solid particle size by hydraulic shear; discharging the slurry to the screen separator with the second slurry pump; and receiving the slurry into one of the first and second equalization tank while discharging the slurry from the other equalization tank.

Aspect 54. The method in accordance with any of aspects 51-53, further comprising juxtaposing a high phosphorus solids tank with the first phase particle separator, and connecting the high phosphorus solids tank in fluid communication with the screen separator and the dissolved carbon air flotation separator; and receiving high phosphorus solid particles greater in size than the predetermined solid particle size into the high phosphorus solids tank.

Aspect 55. The method in accordance with any of aspects 51-54, wherein the electrocoagulation unit further comprises a collection basin having an outlet wall extending between an upper edge and a lower edge, the collection basin having an internal baffle adjacent the outlet wall, the collection basin having a sloping floor; and the method further comprises disposing a first outlet adjacent the outlet wall upper edge and adapting the first outlet for discharging slurry particles smaller than the predetermined solid particle size; disposing a second outlet below the first outlet and adjacent the internal baffle and adapting the second outlet for discharging slurry particles larger than the particles discharged by the first outlet; and disposing a third outlet below the second outlet and adjacent the sloping floor and allowing passage through the third outlet of slurry particles smaller than the predetermined solid particle size and larger than the predetermined solid particle size.

Aspect 56. The method in accordance with any of aspects 51-55, wherein influent entering the dissolved carbon air flotation separator comprises influent slurry, effluent exiting the dissolved carbon air flotation separator comprises feedstock, and slurry exiting the dissolved carbon air flotation separator comprises particles larger than the predetermined solid particle size; and the method further comprises disposing at least one adjusting baffle within the dissolved carbon air flotation separator, and directing the influent slurry to flow through the adjusting baffle; adjusting a cross-sectional flow area of the at least one adjusting baffle, thereby regulating a flow rate of the influent slurry; disposing a separation zone downstream of the adjusting baffle; separating the slurry particles larger than the predetermined solid particle size from the wastewater feedstock particles generally smaller than the predetermined solid particle size within the separation zone; providing at least one sludge hopper downstream of the separation zone, and receiving the slurry particles larger than the predetermined solid particle size, which are sinking, into the sludge hopper; disposing a conveyor with at least one blade above the separation zone, and moving the slurry particles larger than the predetermined solid particle size, which are floating, into the sludge hopper; and conveying the slurry particles larger than the predetermined solid particle size to the first phase particle separator.

Aspect 57. The method in accordance with any of aspects 51-56, wherein the dissolved carbon air flotation separator further comprises a plurality of adjusting baffles and separation zones, the conveyor includes a plurality of blades; and the method further comprises disposing a clear well downstream of the separation zones and receiving feedstock particles generally smaller than the predetermined solid particle size into the clear well; adjusting a cross-sectional flow area of the plurality of adjusting baffles, thereby regulating a flow rate of the influent slurry; causing a residence time and a hydrodynamic trajectory of the influent slurry particles in the separation zones to vary with the flow rate of the influent slurry, thereby causing particles larger than the predetermined solid particle size to separate from the influent flow and move downward, and allowing particles smaller than the predetermined solid particle size to move laterally into the clear well; disposing a plurality of sludge hoppers below the separation zones and receiving downward moving particles into the sludge hoppers; disposing a sludge manifold below the separation zones, connecting the sludge manifold in fluid communication with the sludge hoppers, and receiving particles larger than the predetermined solid particle size into the sludge manifold; disposing a $CO_2$ manifold adjacent the separation zones, connecting the $CO_2$ manifold in fluid communication with the separation zones, and admitting $CO_2$ bubbles into the separation zones; connecting the $CO_2$ manifold in fluid communication with the membrane module, and receiving $CO_2$ into the $CO_2$ manifold from the membrane module; causing slurry particles larger than the predetermined solid particle size to float upward with the $CO_2$ bubbles; disposing a scum hopper adjacent the separation zones, and connecting the scum hopper in fluid communication with the sludge manifold; moving the floating slurry particles larger than the predetermined solid particle size into the scum hopper with the conveyor blades, and conveying the particles to the sludge manifold; connecting the sludge manifold in fluid communication with the screen separator, and conveying the slurry to the screen separator; and conveying effluent with a seeding line from the screen separator to the anaerobic digester; and maintaining an active bacteria culture for digestion by conveying effluent to the anaerobic digester.

Aspect 58. The method in accordance with any of aspects 51-57, wherein the at least one biocurtain further comprises a float pipe, and two sheets of polymeric material spaced apart; the heat exchanger further comprises a tubing heat exchanger disposed between the two sheets; and the method further comprises receiving heat into the heat exchanger from an external heat source, and releasing the heat to the two sheets, thereby promoting growth of the bacteria; forming alternating ridges and furrows on each of the two sheets, thereby increasing the surface area for growth of the bacteria; floating the float pipe upon a surface of the wastewater, and supporting the biocurtain with the float pipe; and extending the sheets downward from the float pipe, and anchoring the sheets to a tank bottom.

Aspect 59. The method in accordance with any of aspects 51-58, wherein the external heat source further comprises the compressor; the tubing heat exchanger further comprises a heat exchange fluid; and the method further comprises absorbing waste heat from the compressor with the heat exchange fluid and releasing the heat to the biocurtain sheets, thereby maintaining the bacteria at an optimum temperature.

Aspect 60. The method in accordance with any of aspects 51-59, wherein the anaerobic digester further comprises a plurality of biocurtains spaced apart along the anaerobic digester; the tubing heat exchanger further comprises a heat exchange fluid; and the method further comprises flowing the feedstock through the digester and around each of the plurality of biocurtains in a serpentine path; absorbing heat from the heat source with the heat exchange fluid and releasing the heat to the biocurtain sheets, thereby maintaining the bacteria at an optimum temperature; and returning the heat exchange fluid to the heat source.

Aspect 61. The method in accordance with any of aspects 51-60, further comprising disposing a plurality of sweep jet nozzles spaced apart along a sweep jet inlet manifold in the anaerobic digester directing the influent across a tank bottom of the anaerobic digester with the nozzles, thereby causing the settled solids to flow across the tank bottom to a settled solids outlet manifold; and disposing a plurality of settled solids nozzles spaced apart along the settled solids outlet manifold, and receiving the settled solids flowing across the tank bottom into the settled solids outlet manifold.

Aspect 62. The method in accordance with any of aspects 51-61, further comprising providing a collection pit and connecting the collection pit in fluid communication with the anaerobic digester and the knock out pot; receiving the effluent into the collection pit from the anaerobic digester; receiving the water into the collection pit from the knock out pot; providing at least one lagoon and connecting the lagoon in fluid communication with the collection pit and the first phase particle separator; and receiving the water into the lagoon from the collection pit, and conveying the water from the lagoon to the first phase particle separator.

Aspect 63. The method in accordance with any of aspects 51-62, wherein the anaerobic digester further comprises a digester first cell having a first cell inlet and a first cell outlet, the first cell being adapted for selective connections upstream and downstream; a digester second cell having a second cell inlet and a second cell outlet, the second cell being adapted for selective connections upstream and downstream; a first cell bypass adapted for selectively connecting the second cell outlet to the first cell inlet; and a second cell bypass adapted for selectively connecting the first cell outlet to the second cell inlet; and the method further comprises selectively connecting the first cell and the second cell in fluid communication with the dissolved carbon air flotation separator and the collection pit in a manner selected from the group consisting of connecting the first cell inlet and the second cell inlet to the dissolved carbon air flotation separator, connecting the first cell outlet and the second cell outlet to the collection pit, and closing the first cell bypass and the second cell bypass; connecting the first cell inlet to the dissolved carbon air flotation separator, connecting the first cell outlet to the collection pit, closing the second cell inlet and the second cell outlet, and closing the first cell bypass and the second cell bypass; connecting the second cell inlet to the dissolved carbon air flotation separator, connecting the second cell outlet to the collection pit, closing the first cell inlet and the first cell outlet, and closing the first cell bypass and the second cell bypass; connecting the first cell inlet to the dissolved carbon air flotation separator, closing the first cell outlet downstream, closing the second cell inlet upstream, connecting the second cell outlet to the collection pit, connecting the second cell bypass between the first cell outlet and the second cell inlet, and closing the first cell bypass; and connecting the second cell inlet to the dissolved carbon air flotation separator, closing the second cell outlet downstream, closing the first cell inlet upstream, connecting the first cell outlet to the collection pit, connecting the first cell bypass between the second cell outlet and the first cell inlet, and closing the second cell bypass.

It will be appreciated that variants of the above-disclosed and other features and functions, or alternatives thereof, may be desirably combined into many other different systems or applications. Various presently unforeseen or unanticipated alternatives, modifications, variations, or improvements therein may be subsequently made by those skilled in the art which are also intended to be encompassed by the following claims.

What is claimed is:

1. An anaerobic waste digestion system for use in connection with a source of waste comprising anaerobically digestible material, for generating methane from the waste by anaerobic digestion using bacteria, the waste being a water-based slurry comprising solid particles having a particle size larger than a predetermined size unsuitable for digestion, the slurry further comprising solid particles having a particle size smaller than a predetermined size suitable for digestion, the anaerobic waste digestion system comprising:
    a first phase particle separator, including a screen separator adapted for receiving the slurry, the screen separator being adapted for removing from the slurry solid particles having the particle size larger than the predetermined size unsuitable for digestion, the first phase particle separator being adapted for allowing passage therethrough of the slurry;
    a second phase particle separator including an electrocoagulation unit connected in fluid communication with the screen separator for electrochemically inducing hydrolysis of the slurry, so as to cause particles to settle out of the slurry, the electrocoagulation unit being adapted for allowing passage therethrough of the slurry;
    a third phase particle separator including a dissolved carbon air flotation (DCAF) separator connected in fluid communication with the electrocoagulation unit, the DCAF separator having a $CO_2$ bubbler for separating by flotation the solid particles having the particle size larger than the predetermined size unsuitable for digestion from the solid particles having the particle size smaller than the predetermined size suitable for digestion, the DCAF separator being adapted for allowing passage therethrough of the solid particles having the particle size smaller than the predetermined size suitable for digestion as feedstock;
    a fourth phase gas producer configured to provide an operating temperature in a range from approximately 68 to 140° F., the fourth phase gas producer including at least one low solids anaerobic digester connected in fluid communication with the DCAF separator, wherein an influent comprising the solid particles having the particle size smaller than the predetermined size suitable for digestion enters the anaerobic digester as feedstock, biogas exits as a product, an effluent exits as wastewater, and a slurry exits as settled solids, the anaerobic digester having at least one biocurtain for growing the bacteria, the anaerobic digester being adapted for allowing passage therethrough of the biogas; and
    a process control operatively connected to the anaerobic waste digestion system for controlling the anaerobic waste digestion system;
    wherein the predetermined size suitable for digestion is less than about 150 μm.

2. The anaerobic waste digestion system of claim 1, wherein the waste is an animal waste comprising bedding sand and manure, and wherein the first phase particle separator further comprises:
    a sand lane for receiving the animal waste, the sand lane adapted for attachment to a source of animal waste and adapted to receive water from a water source, wherein the bedding sand is separated from the animal waste and water to form the water-based slurry;
    an equalization pit connected in fluid communication with the sand lane for receiving the water-based slurry, the equalization pit being adapted for allowing passage therethrough of the slurry to an equalization tank.

3. The anaerobic waste digestion system of claim 1, wherein the first phase particle separator further comprises:
    at least one equalization tank adapted for attachment to the source of waste for receiving the water-based slurry;
    at least one slurry pump connected in fluid communication with the equalization tank, for reducing particle size of the solid particles by hydraulic shear;
    the screen separator being connected in fluid communication with the equalization tank and the slurry pump; and
    a solids tank connected in communication with the screen separator, for receiving solid particles having the particle size larger than the predetermined size unsuitable for digestion.

4. The anaerobic waste digestion system of claim 3, wherein the at least one equalization tank and the at least one slurry pump comprises:
    a first equalization tank;
    a first slurry pump adapted for receiving slurry from the first equalization tank and returning the slurry to the first equalization tank, so as to reduce particle size by hydraulic shear, the first slurry pump being adapted for discharging the slurry to the screen separator;
    a second equalization tank; and
    a second slurry pump adapted for receiving slurry from the second equalization tank and returning the slurry to the second equalization tank, so as to reduce particle size by hydraulic shear, the second slurry pump being adapted for discharging the slurry to the screen separator; wherein
    one of the first and second equalization tank is adapted for receiving slurry while the other equalization tank is discharging.

5. The anaerobic waste digestion system of claim 1, wherein the first phase particle separator further comprises a solids tank for receiving phosphorus-containing solids removed by the screen separator.

6. The anaerobic waste digestion system of claim 1, wherein the electrocoagulation unit further comprises a collection basin including:
    an outlet wall extending between an upper edge and a lower edge;
    an internal baffle adjacent the outlet wall;
    a sloping floor;
    a first outlet disposed adjacent the outlet wall upper edge adapted for discharging solid particles having a particle size smaller than the predetermined size suitable for digestion;
    a second outlet disposed below the first outlet and adjacent the internal baffle, adapted for discharging solid particles having a particle size larger than the particles discharged by the first outlet; and a third outlet disposed below the second outlet and adjacent the sloping floor for discharging solid particles having a particle size smaller than the predetermined size suitable for digestion and solid particles having a particle size larger than the predetermined size suitable for digestion.

7. The anaerobic waste digestion system of claim 1, further comprising:

a fifth phase gas refiner including a membrane module connected in fluid communication with the anaerobic digester for removing heavy hydrocarbons, $CO_2$, and contaminant liquids, the fifth phase gas refiner being adapted for allowing passage therethrough of the biogas.

8. The anaerobic waste digestion system of claim 7, wherein the fifth phase gas refiner further comprises:

a knock out pot connected in fluid communication with the anaerobic digester, the knock out pot being adapted for removing entrained droplets of water from the biogas;

a scrubber connected in fluid communication with the knock out pot for removing water vapor, particulates, and contaminant gas from the biogas; and a compressor connected in fluid communication with the scrubber and the membrane module.

9. The anaerobic waste digestion system of claim 8, further comprising:

a collection pit connected in fluid communication with the anaerobic digester effluent outlet and the knock out pot for receiving the effluent from the anaerobic digester and the water from the knock out pot; and at least one lagoon connected in fluid communication with the collection pit for receiving the effluent and water therefrom, the lagoon being connected in fluid communication with the first phase particle separator for conveying the water thereto.

10. The anaerobic waste digestion system of claim 8, wherein the anaerobic digester further comprises:

a digester first cell having a first cell inlet and a first cell outlet, the first cell being adapted for selective connections upstream and downstream;

a digester second cell having a second cell inlet and a second cell outlet, the second cell being adapted for selective connections upstream and downstream;

a first cell bypass adapted for selectively connecting the second cell outlet to the first cell inlet; and a second cell bypass adapted for selectively connecting the first cell outlet to the second cell inlet;

wherein the first cell and the second cell are selectively connected in fluid communication with the DCAF separator and the collection pit in a manner selected from the group consisting of:

the first cell inlet and the second cell inlet are connected to the DCAF separator, the first cell outlet and the second cell outlet are connected to the collection pit, the first cell bypass and the second cell bypass are closed;

the first cell inlet is connected to the DCAF separator, and the first cell outlet is connected to the collection pit, the second cell inlet and the second cell outlet are closed, the first cell bypass and the second cell bypass are closed;

the second cell inlet is connected to the DCAF separator, and the second cell outlet is connected to the collection pit, the first cell inlet and the first cell outlet are closed, the first cell bypass and the second cell bypass are closed;

the first cell inlet is connected to the DCAF separator, and the first cell outlet is closed downstream, the second cell inlet is closed upstream and the second cell outlet is connected to the collection pit, the second cell bypass is connected between the first cell outlet and the second cell inlet, and the first cell bypass is closed; and the second cell inlet is connected to the DCAF separator, and the second cell outlet is closed downstream, the first cell inlet is closed upstream and the first cell outlet is connected to the collection pit, the first cell bypass is connected between the second cell outlet and the first cell inlet, and the second cell bypass is closed.

11. The anaerobic waste digestion system of claim 7, further comprising a sixth phase pipeline injector for injecting the biogas into a local pipeline system, the sixth phase pipeline injector being connected in fluid communication with the membrane module.

12. The anaerobic waste digestion system of claim 1, wherein influent entering the DCAF separator comprises influent slurry, effluent exiting the DCAF separator comprises feedstock, and slurry exiting the DCAF separator comprises particles having a particle size larger than the predetermined size suitable for digestion, wherein the DCAF separator further comprises:

at least one adjusting baffle disposed so as to cause the influent slurry to flow through the adjusting baffle, and adapted for adjusting cross-sectional flow area, so as to regulate a flow rate of the influent slurry;

a separation zone disposed downstream of the adjusting baffle, wherein the particles having a particle size larger than the predetermined size suitable for digestion are separated from the wastewater feedstock particles which are generally smaller than the predetermined size suitable for digestion;

at least one sludge hopper for removing the slurry particles larger than the predetermined size, which are sinking; and a conveyor with at least one blade for removing the slurry particles larger than the predetermined size, which are floating, wherein the solid particles having a particle size larger than the predetermined size suitable for digestion are returned to the first phase particle separator.

13. The anaerobic waste digestion system of claim 12, wherein the DCAF separator further comprises:

a clear well for receiving feedstock particles generally smaller than the predetermined size suitable for digestion;

a plurality of adjusting baffles and separation zones, the adjusting baffles being adapted to cause a residence time and a hydrodynamic trajectory of the influent slurry particles in the separation zones to vary with the flow rate of the influent slurry so as to cause particles larger than the predetermined size suitable for digestion to separate from the influent flow and move downward, and to allow particles smaller than the predetermined size suitable for digestion to move laterally into the clear well;

a sludge manifold disposed below the separation zones for receiving particles larger than the predetermined size suitable for digestion, the sludge manifold being adapted to convey the slurry particles larger than the predetermined size suitable for digestion to the screen separator;

a plurality of sludge hoppers disposed below the separation zones for directing downward moving particles into the sludge manifold;

a $CO_2$ manifold connected in fluid communication with the separation zones for admitting $CO_2$ bubbles into the separation zones, so as to cause slurry particles larger than the predetermined size suitable for digestion to float upward;

a scum hopper adapted to receive floating slurry particles from the conveyor and convey the particles to the sludge manifold;

the conveyor includes a plurality of blades to move floating slurry particles into the scum hopper; and a seeding line connected in fluid communication between the screen separator and the anaerobic digester to convey effluent to the anaerobic digester, so as to maintain an active bacterial culture for digestion.

14. The anaerobic waste digestion system of claim 13, wherein the $CO_2$ manifold is in fluid communication with the membrane module, so as to receive $CO_2$ from the membrane module.

15. The anaerobic waste digestion system of claim 1, wherein the anaerobic digester further comprises:

a digester tank with first and second opposed sidewalls extending between an inlet endwall and an outlet endwall, the digester tank inlet endwall having an influent inlet in fluid communication with the dissolved carbon air flotation separator, the digester tank outlet endwall having an effluent outlet;

a sweep jet inlet manifold in fluid communication with the influent inlet for moving settled solids particles across the digester tank; and a settled solids outlet manifold for removing settled solids from the digester tank, the settled solids outlet manifold being connected in fluid communication with the sweep jet inlet manifold.

16. The anaerobic waste digestion system of claim 15, wherein the at least one biocurtain further comprises:

a float pipe, which floats upon a surface of the wastewater, so as to support the biocurtain;

two sheets of polymeric material spaced apart, each sheet having alternating ridges and furrows, so as to increase the surface area for bacterial growth, the sheets extending from the float pipe downward to a tank bottom.

17. The anaerobic waste digestion system of claim 16, wherein the anaerobic digester further comprises:

a plurality of biocurtains spaced apart from the inlet endwall to the outlet endwall, every other biocurtain extending from a proximal end adjacent the first sidewall to a distal end adjacent the second sidewall and spaced apart from the second sidewall by a predetermined flow space, each remaining biocurtain extending from a proximal end adjacent the second sidewall to a distal end adjacent the first sidewall and spaced apart from the first sidewall by the flow space, each flow space extending from the tank bottom to the wastewater surface, the biocurtains and spaces alternating so as to provide a flow of feedstock around each of the plurality of biocurtains and through the digester.

18. The anaerobic waste digestion system of claim 17, wherein the anaerobic digester further comprises:

a plurality of sweep jet nozzles spaced apart along the sweep jet inlet manifold, the nozzles being adapted for directing influent across the tank bottom, so as to cause settled solids to flow across the tank bottom to the settled solids outlet manifold; and a plurality of settled solids nozzles spaced apart along the settled solids outlet manifold for receiving settled solids flowing across the tank bottom.

* * * * *